US008685320B2

(12) United States Patent
Ogihara et al.

(10) Patent No.: US 8,685,320 B2
(45) Date of Patent: *Apr. 1, 2014

(54) OXYGENATOR

(75) Inventors: Mitsuaki Ogihara, Fujinomiya (JP);
Hidetaka Nakayama, Fujinomiya (JP);
Kazuhiro Mizoguchi, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 182 days.

This patent is subject to a terminal disclaimer.

(21) Appl. No.: 12/783,889

(22) Filed: May 20, 2010

(65) Prior Publication Data
US 2010/0224559 A1 Sep. 9, 2010

Related U.S. Application Data

(62) Division of application No. 11/655,126, filed on Jan. 19, 2007, now Pat. No. 7,749,435.

(30) Foreign Application Priority Data

Jan. 19, 2006 (JP) ................. 2006-011705

(51) Int. Cl.
*A61M 1/16* (2006.01)
*A61M 1/18* (2006.01)
*A61M 1/34* (2006.01)
*A61M 1/36* (2006.01)
*A61M 1/38* (2006.01)
*B01D 69/08* (2006.01)

(52) U.S. Cl.
USPC ........... 422/46; 604/4.01; 604/6.11; 604/6.14

(58) Field of Classification Search
USPC .................. 604/4.01, 5–5.04, 6.01–6.14; 442/44–48
See application file for complete search history.

(56) References Cited

U.S. PATENT DOCUMENTS 3,668,837 A  6/1972 Gross
3,728,256 A  4/1973 Cooper, IV
(Continued)

FOREIGN PATENT DOCUMENTS

JP    63-267367 A    11/1988
JP    2-213356 A     8/1990
(Continued)

OTHER PUBLICATIONS

Partial European Search Report (in English) issued in corresponding European Patent Application No. 07 00 0984, May 11, 2007; EPO, Munich, DE.

(Continued)

*Primary Examiner* — Adam Marcetich
(74) *Attorney, Agent, or Firm* — Buchanan Ingersoll & Rooney PC

(57) ABSTRACT

An oxygenator which helps avoid bubbles in the blood from being discharged through the blood outlet port of the oxygenator includes a housing, a hollow fiber membrane bundle in the housing and formed by a multiplicity of hollow fiber membranes serving for gas exchange, gas-inlet and gas-outlet ports communicating with gas passages of the hollow fiber membranes, and a blood-inlet and blood-outlet ports. A filter member is provided on a side closer to the blood outlet port of the hollow fiber membrane bundle and serves to catch bubbles in blood. The blood outlet port projects from the housing and a passage enlargement is provided in a vicinity of the end of the blood outlet port closer to the housing and having an increased passage cross-sectional area. The blood passed the filter member is allowed to reach the blood outlet port by being decelerated in the passage enlargement.

8 Claims, 20 Drawing Sheets

(56) References Cited

U.S. PATENT DOCUMENTS

| | | | |
|---|---|---|---|
| 4,297,318 A | | 10/1981 | Raible |
| 4,396,584 A | * | 8/1983 | Burgess et al. ............... 422/310 |
| 4,440,723 A | | 4/1984 | Gordon |
| 4,556,489 A | | 12/1985 | Diettrich, Jr. et al. |
| 4,666,543 A | | 5/1987 | Kawano |
| 4,690,758 A | | 9/1987 | Leonard et al. |
| 4,698,207 A | | 10/1987 | Bringham et al. |
| 4,735,775 A | | 4/1988 | Leonard et al. |
| 4,743,371 A | | 5/1988 | Servas et al. |
| 4,784,768 A | | 11/1988 | Mathieu |
| 4,876,066 A | | 10/1989 | Bringham et al. |
| 4,923,679 A | | 5/1990 | Fukasawa et al. |
| 4,948,560 A | | 8/1990 | Deguchi et al. |
| 5,039,486 A | | 8/1991 | Gordon |
| RE33,932 E | * | 5/1992 | Fukasawa et al. ............. 422/46 |
| 5,149,318 A | | 9/1992 | Lindsay |
| 5,162,102 A | * | 11/1992 | Nogawa et al. ................. 422/48 |
| 5,225,161 A | | 7/1993 | Mathewson et al. |
| 5,230,862 A | * | 7/1993 | Berry et al. ...................... 422/48 |
| 5,411,705 A | | 5/1995 | Thor et al. |
| 5,578,267 A | | 11/1996 | Cosentino et al. |
| 5,698,161 A | * | 12/1997 | Montoya ......................... 422/48 |
| 5,762,868 A | | 6/1998 | Leonard |
| 5,770,149 A | * | 6/1998 | Raible ............................. 422/46 |
| 5,817,278 A | * | 10/1998 | Fini et al. ........................ 422/45 |
| 5,817,279 A | | 10/1998 | Eilers et al. |
| 6,113,782 A | * | 9/2000 | Leonard ................... 210/321.89 |
| 6,402,818 B1 | | 6/2002 | Sengupta |
| 6,503,225 B1 | | 1/2003 | Kirsch et al. |
| 6,503,451 B2 | | 1/2003 | Ikeda et al. |
| 6,613,281 B2 | * | 9/2003 | Filho et al. ...................... 422/46 |
| 6,682,698 B2 | | 1/2004 | Chambers et al. |
| 2002/0110485 A1 | | 8/2002 | Stringer et al. |
| 2003/0028073 A1 | * | 2/2003 | Mochizuki et al. ............. 600/16 |
| 2003/0039582 A1 | * | 2/2003 | Chambers et al. .............. 422/44 |
| 2004/0000232 A1 | | 1/2004 | Van Horne et al. |
| 2004/0052681 A1 | * | 3/2004 | Mortensen et al. ............. 422/45 |
| 2004/0175292 A1 | * | 9/2004 | Ghelli et al. .................... 422/45 |
| 2004/0223873 A1 | * | 11/2004 | Maianti et al. .................. 422/46 |
| 2005/0077225 A1 | | 4/2005 | Usher et al. |
| 2006/0016743 A1 | | 1/2006 | Ogihara et al. |
| 2007/0166189 A1 | | 7/2007 | Ogihara |
| 2007/0231203 A1 | | 10/2007 | Mizoguchi et al. |

FOREIGN PATENT DOCUMENTS

| | | |
|---|---|---|
| JP | 7-328114 A | 12/1995 |
| JP | 8-19601 A | 1/1996 |
| JP | 11-137671 A | 5/1999 |
| WO | WO 00/06357 A1 | 2/2000 |

OTHER PUBLICATIONS

Extended European Search Report dated Jul. 27, 2007.
Office Action issued Mar. 9, 2010 by the European Patent Office in European Patent Application No. 07 000 984.0.
Online encyclopedia, "oxygenator" accessed Nov. 4, 2008. http://en.wikipedia.org/wiki/Oxygenator.
European Search Report dated Mar. 8, 2011, issued in corresponding European Patent Application No. 10178879.

* cited by examiner

OXYGENATOR

CROSS-REFERENCE TO RELATED APPLICATIONS

This application is a divisional of U.S. application Ser. No. 11/655,126 filed on Jan. 19, 2007 which claims priority to Japanese Application No. 2006-011705 filed on Jan. 19, 2006, the entire contents of which are incorporated herein by reference.

TECHNICAL FIELD

The present invention relates to oxygenators.

BACKGROUND DISCUSSION

There are known oxygenators constructed to perform gas exchange by use of a multiplicity of hollow fiber membranes. U.S. Pat. No. 6,503,451 describes an example of such an oxygenator.

This oxygenator includes a housing, a hollow fiber membrane bundle received in the housing, blood-inlet and blood-outlet ports, and gas-inlet and gas-outlet ports so that gas exchange, i.e. oxygenation and carbon dioxide removal, is performed between the blood and gas through the hollow fiber membranes.

In oxygenators, it is possible for bubbles to exist in the blood coming entering the blood inlet port. In such a case, bubbles should preferably be removed by the hollow fiber membrane bundle.

However, the hollow fiber membrane bundle is designed to efficiently effect gas exchange and is not specifically designed or intended to remove bubbles. Thus, a problem exists in that bubbles are not fully removed by the hollow fiber membrane bundle. As a result, bubbles remaining in the blood are discharged out of the blood outlet port and carried with the blood downstream of the oxygenator. For this reason, it is a known practice to provide an arterial filter on an arterial line between the oxygenator and the patient for purposes of removing bubbles.

SUMMARY

An oxygenator comprises a housing having an interior, a blood inlet port in the housing through which blood is adapted to flow, with the blood inlet port opening to outside the housing and communicating with the interior of the housing to introduce the blood into the interior of the housing, a hollow fiber membrane bundle positioned in the interior of the housing and comprised of a multiplicity of integrated hollow fiber membranes configured to subject the blood introduced into the housing to gas exchange, with the hollow fiber membranes each possessing a lumen extending between opposite ends of the hollow fiber membrane forming a gas passage for passage of gas, and a gas inlet port in the housing through which gas is adapted to flow, with the gas inlet port opening to outside the housing and communicating with the gas passages of the hollow fiber membranes to introduce the gas into the gas passages. A gas outlet port in the housing through which gas is adapted to flow opens to outside the housing and communicates with the gas passages of the hollow fiber membranes to discharge the gas in the gas passages, and a blood outlet port in the housing through which blood which has been subjected to the gas exchange is adapted to flow opens to outside the housing and communicates with the interior of the housing to discharge from the housing the blood which has been subjected to the gas exchange. A filter member is positioned at a side of the hollow fiber membrane bundle closer to the blood outlet port and is constructed to catch bubbles in the blood which has been subjected to the gas exchange, and a passage enlargement is provided in a vicinity of an end of the blood outlet port closer to the housing and possessing an increased passage cross-sectional area so that blood which has passed through the filter member toward the blood outlet port is decelerated in the passage enlargement.

Because blood is decelerated in the passage enlargement, the bubbles trapped by the filter are prevented from being carried in blood to the blood outlet port. The bubbles in the blood can thus be prevented from going out of the blood outlet.

According to another aspect, an oxygenator comprises a housing having an interior, a blood inlet port in the housing through which blood is adapted to flow, with the blood inlet port opening to outside the housing and communicating with the interior of the housing to introduce the blood into the interior of the housing, a hollow fiber membrane bundle positioned in the interior of the housing and comprised of a multiplicity of integrated hollow fiber membranes configured to subject the blood introduced into the housing to gas exchange, wherein the hollow fiber membranes each possess a lumen extending between opposite ends of the hollow fiber membrane forming a gas passage for passage of gas, a gas inlet port in the housing through which gas is adapted to flow, with the gas inlet port opening to outside the housing and communicating with the gas passages of the hollow fiber membranes to introduce the gas into the gas passages, a first gas outlet port in the housing through which gas is adapted to flow, with the first gas outlet port opening to outside the housing and communicating with the gas passages of the hollow fiber membranes to discharged the gas in the gas passages, and a blood outlet port in the housing through which blood which has been subjected to the gas exchange is adapted to flow, wherein the blood outlet port opens to outside the housing and communicates with the interior of the housing to discharge from the housing the blood which has been subjected to the gas exchange. A bubble filter member is positioned at a side of the hollow fiber membrane bundle closer to the blood outlet port and is constructed to catch bubbles in the blood which has been subjected to the gas exchange, and a gas outlet hollow fiber membrane layer is positioned between the hollow fiber membrane bundle and the filter member, with the gas outlet hollow fiber membrane layer comprising a multiplicity of hollow fiber membranes each possessing a lumen. A second gas outlet port in the housing through which bubbles removed by the filter member gas are adapted to flow opens to outside the housing and communicates with the lumens of the hollow fiber membranes forming the gas outlet hollow fiber membrane layer to discharge the bubbles.

In accordance with another aspect, a method of performing gas exchange for blood comprises introducing blood into a housing in which are positioned a plurality of hollow fiber membranes each having a lumen so that the blood flows exteriorly of the hollow fiber membranes, introducing gas into the lumens of the hollow fiber membranes to subject the blood flowing exteriorly of the hollow fiber membranes to gas exchange with the has flowing through the lumens of the hollow fiber membranes, removing bubbles in the blood while the blood is in the housing and after the blood has been subjected to the gas exchange, decelerating the blood from which bubbles have been removed as the blood approaches a blood outlet port in the housing, and discharging the blood which has been decelerated from the housing by way of the blood outlet port.

BRIEF DESCRIPTION OF THE DRAWING FIGURES

DETAILED DESCRIPTION

Figure 1:
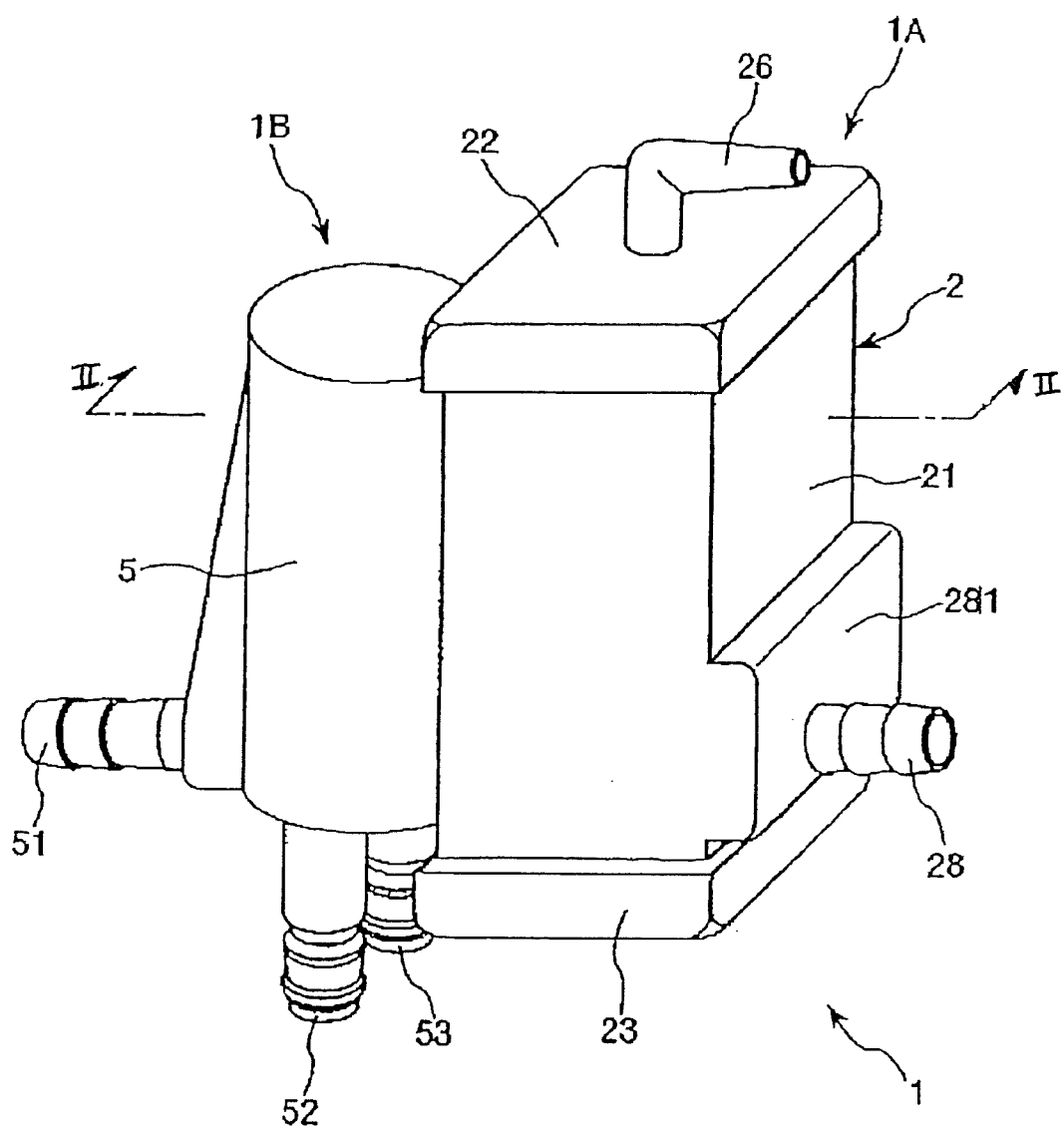
FIG. 1 is a perspective view of a first embodiment of an oxygenator disclosed herein.
Figure 2:
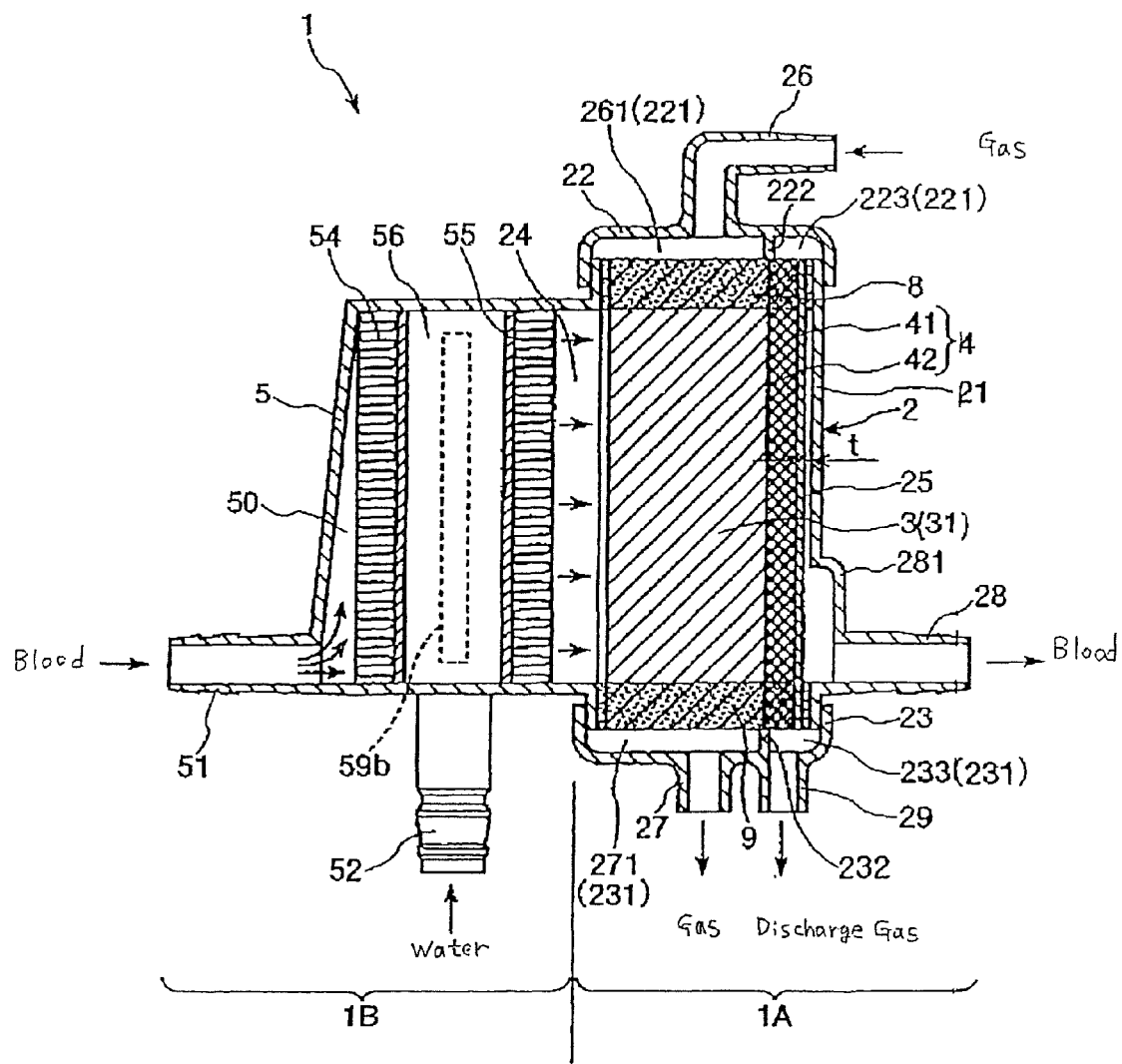
FIG. 2 is a cross-sectional side view of the oxygenator shown in FIG. 1 taken along the section line II-II in FIG. 1.

FIGS. 1-4 illustrate various features associated with one disclosed embodiment of an oxygenator as disclosed herein. In FIGS. 1 and 2, the upper side is referred to as "upper" or "above", the lower side is referred to as "lower" or "below", the left side is referred to as "blood inlet side" or "upstream side", and the right side is referred to as "blood outlet side" or "downstream side".

The oxygenator 1 in the illustrated embodiment is a heat exchanger-equipped oxygenator that includes an oxygenating part 1A adapted to perform gas exchange on blood and a heat exchanging part (heat exchanger) 1B adapted to perform heat exchange on blood. This oxygenator can be set up on a blood extracorporeal circulation circuit, for example.

The oxygenator 1 comprises a housing 2 located on the side of the oxygenating part 1A, and a housing 5 located on the side of the heat exchanger part 1B. The two housings 2, 5 are united or integrated together as a single unitary body.

The housing 2 of the oxygenator part 1A is comprised of a cylindrical housing body 21 quadrilateral (rectangle or square) in cross-section (hereinafter, referred to as a "rectangular cylindrical housing body"), a first header (upper lid) 22 that closes the upper opening of the rectangular cylindrical housing body 21, and a second header (lower lid) 23 that closes the lower opening of the rectangular cylindrical housing body 21. Both the first header 22 and second header 23 are dish-shaped, including a plate-shaped portion with a projecting or upstanding wall extending around the periphery of the plate-shaped portion.

The rectangular cylindrical housing body 21, the first header 22 and the second header 23 can each be formed of a resin material, e.g. polyolefin such as polyethylene or polypropylene, an ester resin (e.g. polyester such as polyethylene terephthalate or polybutylene terephthalate), a styrene resin (e.g. polystyrene, MS resin or MBS resin) or polycarbonate, ceramics materials of various kinds or a metal material. The first and second headers 22, 23 are secured in a liquid-tight manner to the rectangular cylindrical housing body 21 by joining, for example by fusion or an adhesive.

Figure 3:
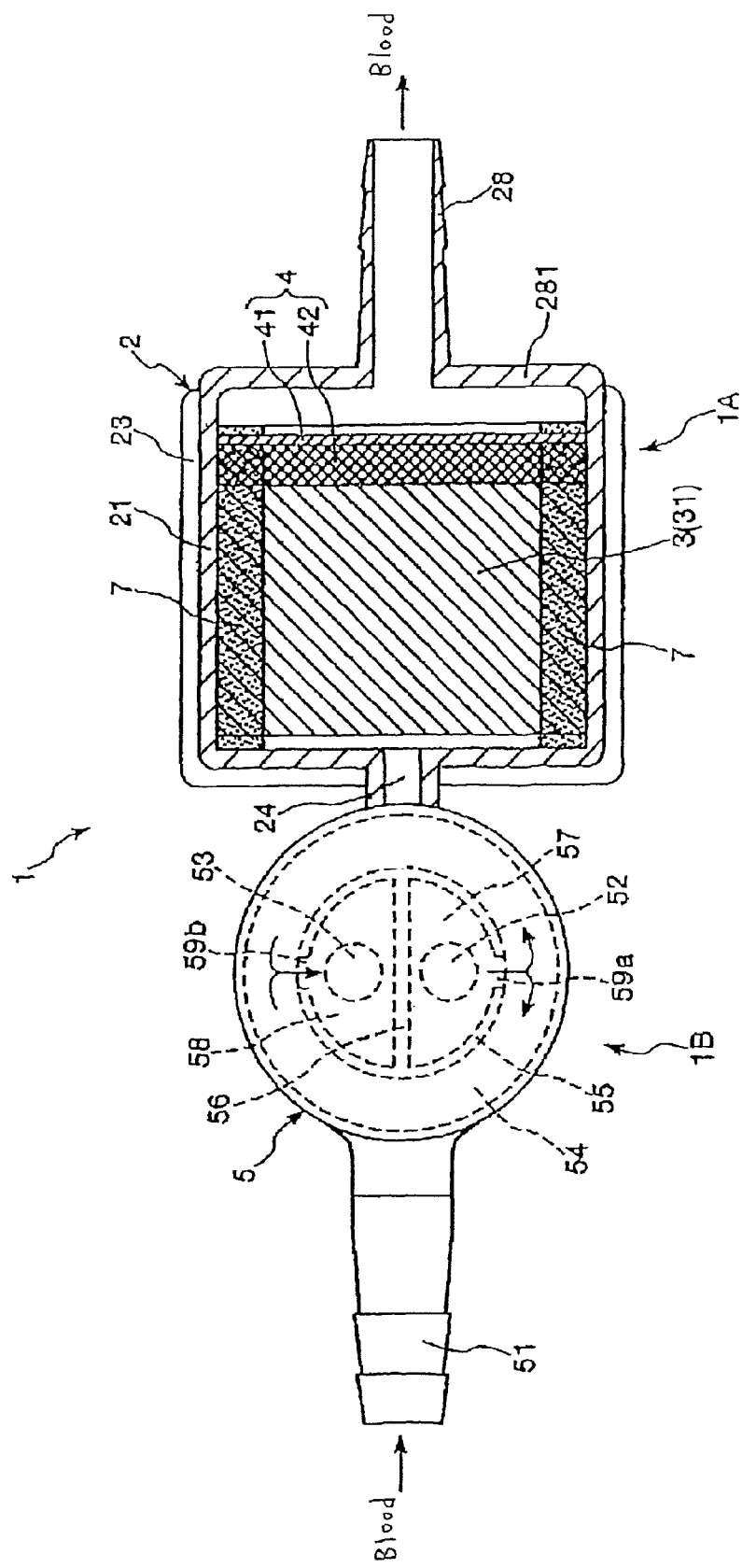
FIG. 3 is a top view partly in cross-section of the oxygenating part of the oxygenator shown in FIG. 1.

The rectangular cylindrical housing body 21 is formed with a tubular blood outlet port 28 projecting from the lower region of the blood outlet side thereof. A passage enlargement 281 possessing a box-shaped form is provided around the blood outlet port 28 closer to the rectangular cylindrical housing body 21 (housing 2), i.e., at and around the upstream end of the blood outlet port 28. The blood outlet port 28 has a lumen in communication with the interior (a lumen) of the passage enlargement 281, thus forming a passage through which the blood which has passed through a filter member 41, described in more detail below, is to pass. As shown in FIGS. 2 and 3, the passage enlargement 281 is provided as a region where the passage increases in cross-sectional area relative to the blood outlet port 28.

In the oxygenator 1, the blood passing through the filter member 41 reaches the blood outlet port 28 in a state in which the blood has been decelerated by the passage enlargement 281.

A tubular gas inlet port 26 projects from the upper surface of the first header 22. A tubular gas outlet port 27 and a tubular gas outlet port 29 project from the lower surface of the second header 23. The gas inlet port 26 has an intermediate portion that is bent nearly perpendicularly so that the tip end portion of the gas inlet port 26 is parallel with the blood outlet port 28.

It is to be understood that the housing 2 need not necessarily be a perfect rectangular parallelepiped in form over its entirety in that it may be chamfered or rounded partly or entirely at corners or may be in a form partly cut away or added with a different-shaped part.

Figure 4:
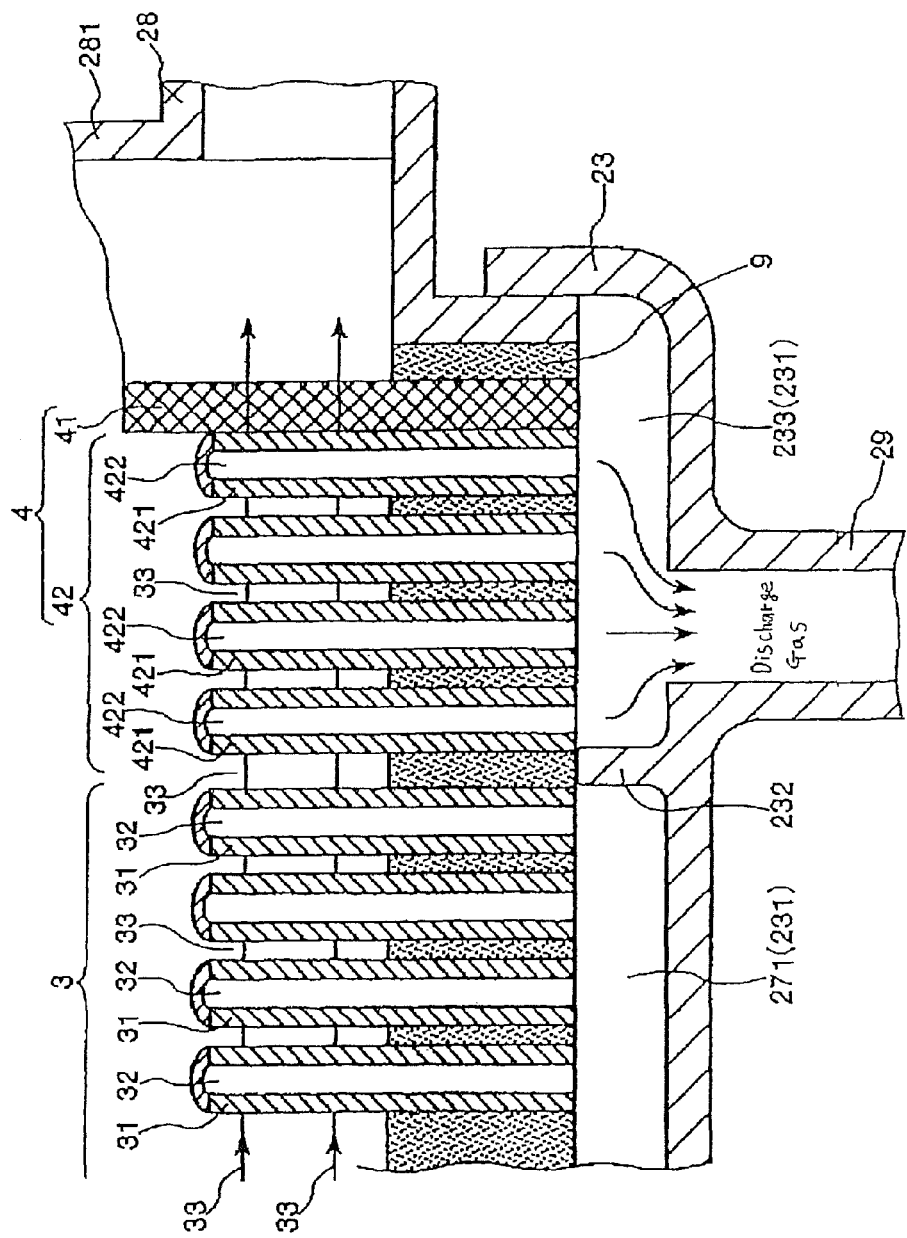
FIG. 4 is an enlarged cross-sectional view of a lower right region (fixing region of the hollow fiber membrane bundle, filter member and gas outlet hollow fiber membrane layer) of the oxygenator shown in FIG. 2.

Positioned in the housing 2 is a hollow fiber membrane bundle 3 formed by integrating a multiplicity of hollow fiber membranes 31 which function to carry out gas exchange, a filter member 41 serving as bubble removal means 4 provided on the blood outlet port 28 (blood outlet portion) side of the hollow fiber membrane bundle 3, and a gas outlet hollow fiber membrane layer 42, as shown in FIGS. 2-4. The hollow fiber membrane bundle 3, the filter member 41 layers and gas outlet hollow fiber membrane layer 42 are arranged in that order, with the hollow fiber membrane bundle 3 being located closer to the blood inlet side.

As shown in FIG. 4, almost all the hollow fiber membranes 31 forming the hollow fiber membrane bundle 3 are arranged nearly parallel with one another. In this case, the lengthwise direction of the hollow fiber membranes 31 are arranged vertically.

Incidentally, the arrangement pattern, direction, etc. of the hollow fiber membranes 31 of the hollow fiber membrane bundle 3 are not limited to those mentioned but may be, for example, in a structure in which the hollow fiber membranes 31 are arranged horizontally, a structure in which the hollow fiber membranes 31 obliquely intersect one another at intersections, a structure in which all or some of the hollow fiber membranes 31 are arranged curved, or a structure in which all or some of the hollow fiber membranes 31 are arranged in a corrugated, helical, spiral or annular manner.

The hollow fiber membranes 31 have opposite ends fixed to the inner surfaces of the rectangular cylindrical housing body 21 by way of partitioning walls 8, 9 as shown in FIG. 2. The partitioning walls 8, 9 are formed of a potting material, e.g. polyurethane or silicone rubber.

The hollow fiber membrane bundle 3 has opposite ends, in the widthwise direction, that are respectively fixed (secured) to the inner surfaces of the rectangular cylindrical housing body 21 through a setting member 7 as shown in FIG. 3. The setting member 7 may be formed of a material similar to the material (potting material) of the partitioning wall 8, 9 or of another material.

A first chamber 221 is defined by the first header 22 and the partitioning wall 8. The first chamber 221 is divided, by way of a partition 222, into a gas inlet chamber 261 closer to the hollow fiber membrane bundle 3 and a small space 223 closer to the gas outlet hollow fiber membrane layer 42. The partition 222 is positioned, relative to a side-to-side direction (left-to-right direction in FIG. 2), in a boundary between the hollow fiber membrane bundle 3 and the gas outlet hollow fiber membrane layer 42. The hollow fiber membranes 31 have respective upper openings in communication with the gas inlet chamber 261.

A second chamber 231 is also defined by the second header 23 and the partitioning wall 9. The second chamber 231 is divided, by way of a partition wall 232, into a gas outlet chamber 271 closer to the hollow fiber membrane bundle 3 and a small space 233 closer to the gas outlet hollow fiber membrane layer 42. The partition 232 is positioned, relative to a side-to-side direction (left-to-right direction in FIG. 2), in a boundary between the hollow fiber membrane bundle 3 and the gas outlet hollow fiber membrane layer 42. The hollow fiber membranes 31 have respective lower openings in communication with the gas outlet chamber 271 as shown in FIG. 4.

The hollow fiber membranes 31 each have a lumen forming a gas passage 32 through which gas is adapted to flow. The gas inlet port 26 and the gas inlet chamber 261 constitute a gas inlet portion in communication with the gas passages 32 at an upstream end of the gas passages. The gas outlet port 27 and the gas outlet chamber 271 constitute a gas outlet portion in communication with the gas passages 32 at a downstream end of the gas passages.

The hollow fiber membrane bundle 3 is fully positioned in the rectangular cylindrical housing body 21 and is sized and configured in such a way that the hollow fiber membrane bundle 3 possesses a rectangular parallelepiped form and occupies a majority of the space in the housing body interior.

The hollow fiber membranes 31 are exposed between the partitioning walls 8, 9 within the housing 2. A blood passage 33 is formed exterior of the hollow fiber membranes 31 (and also the gas outlet hollow fiber membranes 421 discussed in more detail below). That is, a the blood passage 33 exists at gaps between the hollow fiber membranes 31, allowing the blood to flow from left to right in FIG. 2.

A blood inlet aperture (blood inlet space) 24 is formed as a blood inlet portion at the upstream end of the blood passage 33 (at the upstream end of the hollow fiber membrane bundle 3 in a side-to-side direction). The blood inlet aperture 24 communicates with the blood passage 33 and possesses an elongated (e.g., strip-shaped) form extending vertically (nearly parallel with the longitudinal extent of the hollow fiber membranes 31). The blood inlet aperture 24 is formed in a connection between the rectangular cylindrical housing body 21 and the heat exchanger housing 5. Thus, the interior of the housing 2 is in communication with the interior of the heat exchanger housing 5, through the blood inlet aperture 24. This structure allows for a relatively efficient transfer of blood from the heat exchanging part 1B to the oxygenating part 1A.

The blood inlet aperture 24 preferably has a length (vertical length as seen with reference to FIG. 2) equal to or greater than 70% of the effective length of the hollow fiber membrane 31 (i.e., the length between the lower face of the partitioning wall 8 and the upper face of the partitioning wall 9), with the length of the blood inlet aperture 24 preferably being no greater than the effective length of the hollow fiber membrane 31. In the illustrated embodiment, the length of the blood inlet aperture 24 is equal to the effective length of the hollow fiber membrane 31. This disclosed length of the blood inlet aperture 24 allows for relatively efficient transfer of blood from the heat exchanging part 1B to the oxygenating part 1A and for gas exchange of blood in the blood passage 33.

At least at the upstream end of the blood passage 33 (closer to the blood inlet aperture 24), the blood flows in a direction orthogonal to the lengthwise extent of the hollow fiber membranes 31. This allows for relatively efficient gas exchange of the blood flowing through the blood passage 33.

At the downstream end of the blood passage 33 closer to the downstream portion of the hollow fiber membrane bundle 3, a gap is formed between a filter member 41 (described in more detail below) and the inner surface of the rectangular cylindrical housing body 21. The gap is located where the blood which has passed through the filter member 41 is to flow, thus forming a blood outlet aperture (blood outlet space) 25. A blood outlet portion is formed by the blood outlet aperture 25, the passage enlargement 281 and the blood outlet port 28 communicating with the blood outlet aperture 25 though the passage enlargement 281. The blood outlet aperture 25 or gap has a constant width-wise dimension represented as "t."

With the blood outlet aperture 25, the blood outlet portion is provided with a space where the blood transmitted through the filter member 41 flows toward the blood outlet port 28, thus discharging the blood relatively smoothly.

The hollow fiber membrane bundle 3, the filter member 41, the gas outlet hollow fiber membrane layer 42 and the blood passage 33 are positioned between the blood inlet aperture 24 and the blood outlet aperture 25.

By way of example, the hollow fiber membranes 31 is made of a porous gas-exchange film. Also by way of example, the porous hollow fiber membranes can possess an inner diameter of approximately 100-1000 µm, a wall thickness of approximately 5-200 µm, more preferably 10-100 µm, a porosity of approximately 20-80%, more preferably approximately 30-60%, and a pore size of approximately 0.01-5 µm, more preferably approximately 0.01-1 µm.

The hollow fiber membrane 31 can be made of a hydrophobic polymer material, e.g. polypropylene, polyethylene, polysulfone, polyacrylonitrile, polytetrafluoroethylene or polymethyl pentane. Polyolefin resin is preferred, and polypropylene is more preferred. Pores are preferably formed in the wall of the material by, for example, stretching or solid-liquid phase separation.

The hollow fiber membranes 31 of the hollow fiber membrane bundle 3 have a length (effective length) that is not particularly limited, but is preferably approximately 30-150 mm, more preferably approximately 50-100 mm.

Similarly, the thickness of the hollow fiber membrane bundle 3 (horizontal length or dimension in FIG. 2) is not specifically limited, though is preferably approximately 10-100 mm, more preferably approximately 20-80 mm.

The width of the hollow fiber membrane bundle 3 (vertical dimension or length in FIG. 3) is also not particularly limited, but is preferably approximately 10-100 mm, more preferably approximately 20-80 mm.

As described previously, a bubble removal means 4 is provided at a position downstream of the hollow fiber membrane bundle 3 (closer to the blood outlet portion). The bubble removal means 4 functions to catch bubbles in blood and discharge the caught bubbles to the outside of the blood passage. The bubble removal means 4 comprises a filter member 41 and a gas outlet hollow fiber membrane layer 42 arranged upstream of the filter member 41. The filter member 41 catches bubbles existing in the blood flowing along the blood passage 33. The gas outlet hollow fiber membrane layer 42 is formed by integrating a multiplicity of gas outlet hollow fiber membranes 421 (hereinafter referred to as hollow fiber membranes 421) which transmit and discharge the bubble-forming gas captured at the filter member 41. In the description below, the gas that forms the bubbles caught at the filter member 41 is referred to as "bubble gas".

The filter member 41 is formed by a flat sheet member nearly in a rectangular form (hereinafter also referred to as a "sheet"). The filter member 41 is fixed in the housing 2 by being secured at its edges (four sides) through use of the partitioning walls 8, 9 and the respective setting members 7.

The filter member 41 is positioned by placing its one surface in contact with the downstream surface portion (closer to the blood outlet portion) of the gas outlet hollow fiber membrane layer 42, thus covering nearly all the surface portion. The filter member 41 thus has an increased effective area so that it is possible to relatively fully exhibit the capability of catching bubbles. Also, by increasing the effective area of the filter member 41, even if clogging (e.g., adhesion of blood aggregates) occurs in a part of the filter member 41, it is possible to inhibit or prevent the filter member 41 from being wholly obstructed to blood flow.

The filter member 41 may be, for example, in a mesh form or of a woven fabric, a non-woven fabric or a combination thereof. Of these, a mesh form for the filter member 41 is preferred, particularly a screen filter. This makes it possible to catch bubbles more positively and to pass blood relatively easily.

In the case of the filter 41 being in a mesh form, the mesh size is not limited but is usually preferably 80 µm or smaller, more preferably approximately 15-60 µm, further preferably 20-45 µm. This makes it possible to catch comparatively fine bubbles without increasing the passage resistance to blood, thus providing a quite high catch efficiency of bubbles (i.e., bubble removal capability).

The filter member 41 can be made of a material, e.g. polyolefin such as polyamide, polyethylene or polypropylene, polyester such as polyethylene terephthalate, or polybutylene terephthalate, nylon, cellulose, polyurethane, or an aramid fiber. It is preferable to use polyethylene terephthalate, or polyethylene, polyurethane due to its relatively excellent resistance to blood clotting and the capability of being less clogged.

Meanwhile, the filter member 41 preferably possesses hydrophilicity. That is, the filter member 41 is preferably made itself of a hydrophilic material or has been subjected to a hydrophilizing processing (e.g. plasma processing). This makes it relatively easy to remove bubbles upon priming the oxygenator 1. Also, when blood mixed with bubbles passes through, it is difficult for the bubbles to pass through, thus improving the bubble removal capability at the filter member 41 and helping positively prevent or inhibit the bubbles from flowing out of the blood outlet port 28.

The filter member 41 may be made of one sheet (particularly, a mesh form like a screen filter) or a lamination of two or more sheets. In the case of a lamination of two or more sheets, the sheets forming the filter member are preferably different in at least one of the conditions of their forms, the material(s) forming the sheets, the mesh sizes of the sheets, the flatness/non-flatness of the sheets, the plan shapes of the sheets, etc.

As mentioned, between the filter member 41 and the interior surface of the housing 2, a gap (i.e., blood outlet aperture 25) is formed as shown in FIGS. 2-4). This can help suppress the filter member 41 from coming into direct (close) contact with the inner surface of the housing 2. Thus, the blood passing through the filter member 41 is allowed to easily flow down the blood outlet aperture 25, and then to the blood outlet port 28 relatively smoothly via the passage enlargement 281.

The filter member 41 should preferably closely contact the gas outlet hollow fiber membrane layer 42.

With the arrangement of the filter member 41, even where bubbles exist in the blood flowing along the blood passage 33, such bubbles can be caught thereby inhibiting or preventing bubbles from going out of the blood outlet port 28. This reduces or eliminates the need for an arterial filter conventionally provided in the arterial line.

The bubbles caught by the filter member 41 are removed by the gas outlet hollow fiber membrane layer 42 located upstream of the filter member 41 (located between the filter member 41 and the hollow fiber membrane bundle 3).

As shown in FIG. 4, the hollow fiber membranes 421 forming the gas outlet hollow fiber membrane layer 42, are arranged nearly parallel with the hollow fiber membranes 31 forming the hollow fiber membrane bundle 3. The hollow fiber membranes 421 have both ends (upper and lower ends) fixed to the inner surfaces of the rectangular cylindrical housing body 21 by way of the partitioning walls 8, 9 as shown in FIG. 2, similar to the hollow fiber membranes 31.

Thus, both ends of both the hollow fiber membranes 421 and the hollow fiber membranes 31 can be fixed by way of the partitioning walls 8, 9. The number of process steps can thus be reduced in the manufacture of an oxygenator 1. In addition, the hollow fiber membranes 421 can be fully positioned within the rectangular cylindrical housing body 21. That is, a high charging efficiency of the hollow fiber membranes 421 is available in the rectangular cylindrical housing body 21 (with less dead space). This contributes to the size reduction and performance improvement of the oxygenating part 1A.

As shown in FIG. 3, the gas outlet hollow fiber membrane layer 42 is fixed (secured) at both of its widthwise ends to the inner surfaces of the rectangular cylindrical housing body 21 by the setting members 7.

The hollow fiber membranes 421 each have a lumen forming a gas passage 422 through which is adapted to flow bubble gas entering through a multiplicity of fine pores formed in the wall of the hollow fiber membrane 421.

The gas passages 422 (hollow fiber membranes 421) have upper openings which open into and communicate with the small space 223. Thus, the small space 223 serves as a bubble reservoir that temporarily stores the bubble gas rising from the gas passages 422.

The gas passages 422 also have lower openings which open into and communicate with the small space 233 as shown in FIG. 4. The small space 233 is in communication with the gas outlet port 29.

With this structure, the bubble gas exiting at the lower openings of the gas passages 422 passes into the small space 233 and then the gas outlet port 29 so that is permitted to positively exit out of the oxygenator 1 (housing 2). This makes it possible to inhibit or prevent bubbles in the blood passing along the blood passage 33 from going out of the blood outlet portion. The gas outlet port 29 can be considered to function as a part of the bubble removal means 4.

The hollow fiber membranes 421 constituting the gas outlet hollow fiber membrane layer 42 and the hollow fiber membranes 31 constituting the hollow fiber membrane bundle 3 may be the same or different in type.

In the case of the hollow fiber membranes 421 and the hollow fiber membranes 31 being different in type, they are preferably different in at least one of material, property and arrangement conditions.

By way of example, the gas outlet hollow fiber membrane layer 42 can possess a thickness (horizontal length in FIG. 2) of approximately 10-50 mm.

The gas outlet hollow fiber membrane layer 42 can also possess a width (vertical length in FIG. 3) of approximately 10-80 mm.

The arrangement pattern, direction, etc. of the hollow fiber membranes 421 in the gas outlet hollow fiber membrane layer 42 may be such as to form a structure in which the hollow fiber membranes 421 are arranged horizontally, a structure in which the hollow fiber membranes 421 have obliquely intersecting points (intersections) of one with another, a structure in which all or part of the hollow fiber membranes 421 are arranged in a curved manner, or a structure in which all or part of the hollow fiber membranes 421 are arranged in a corrugated, helical, spiral or annular manner.

With the aspects of the oxygenator described above, a number of effects can be achieved. For example, gas exchange can be positively made by the hollow fiber membrane bundle 3, with the bubbles in the gas-exchanged blood being positively removed by the gas outlet hollow fiber membrane layer 42. Conditions can be selected for the hollow fiber membrane bundle 3 suitable for gas exchange while conditions can be selected for the hollow fiber membrane layer 42 suitable for gas removal. Therefore, a relatively high performance can be exhibited in both gas exchange and gas removal. Further, the structure having both performances of gas exchange and gas discharge can be received efficiently within the one housing 2, thus keeping the interval (charge amount) in the blood passages 33 relatively small.

The bubbles in the blood containing bubbles that lies upstream of the filter member 41 (hereinafter, such blood is referred to as "bubble-containing blood") are adapted to be caught at the filter member 41. The blood which has passed the filter member 41 and been subjected to bubble removal flows toward the blood outlet port 28. By sufficiently reducing the velocity of the blood entering the passage enlargement 281, the blood moving toward the blood outlet port 28 is prevented from entraining (against venturi effect), across the filter member 41, the bubbles caught by the filter member 41. This can help assist in positively preventing the bubbles of the blood from passing out of the blood outlet port 28.

The description which follows describes aspects of the heat exchanging part (heat exchanger) 1B. The heat exchanger 1B includes the heat exchanger housing 5 which possesses a nearly cylindrical form having upper and lower closed ends. A blood chamber 50 is formed inside the heat exchanger housing 5. A tubular heating medium inlet port 52 and a tubular heating medium outlet port 53 extend from the heat exchanger housing 5 at the lower end (lower surface) of the heat exchanger housing 5. A tubular blood inlet port 51 projects in the lower left region of the heat exchanger housing 5 in FIG. 2. The blood inlet port 51 has a lumen in communication with the blood chamber 50.

Arranged in the interior of the heat exchanger housing 5 are a heat exchange element 54 that is cylindrical in form, a heating medium chamber-forming member (cylindrical wall) 55 having a cylindrical form and positioned along the inner periphery of the heat exchange element 54, and a partitioning wall 56 separating the inner space of the heating medium chamber-forming member 55 into an inlet heating medium chamber 57 and an outlet heating medium chamber 58. The heating medium chamber-forming member 55 serves to form a heating medium chamber that temporarily stores the heating medium at the inside of the heat exchange element 54 and to help prevent the cylindrical heat exchange element from deforming.

The heating medium chamber-forming member 55 and the partitioning wall 56 are appropriately fixed in the heat exchanger housing 5, for example by bonding through fusion or an adhesive. The heating medium chamber-forming member 55 and the partitioning wall 56 may be formed as separate members or may be integrally formed together as a single unitary one-piece body.

Elongated (strip-formed) openings 59a, 59b are formed in the heating medium chamber-forming member 55. These openings 59a, 59b extend vertically and penetrate through the wall of the heating medium chamber-forming member 55. The openings 59a, 59b are arranged at opposite positions through the partitioning wall 56 as illustrated in FIG. 3. The opening 59a communicates with the inlet heating medium chamber 57 while the opening 59b communicates with the outlet heating medium chamber 58.

The heat exchange element 54 can be in the form of a so-called bellows-type heat exchange element (bellows tube) as shown in FIG. 2. The bellows-type heat exchange element 54 comprises a bellows-formed central portion and a cylindrical portion at each end (upper and lower ends). The bellows-formed central portion is comprised of a multiplicity of hollow annular projections that are parallel (inclusive of nearly parallel) to one another so as to form a plurality of closely arranged undulations. The inner diameter of each cylindrical end portion is equal to (inclusive of nearly equal to) the inner diameter of the bellows-formed central portion. The heat exchange element 54 can be formed of a metal material such as stainless steel or aluminum, or a resin material such as polyethylene or polycarbonate, for example. It is preferable to use a metal material, such as stainless steel or aluminum for reasons of strength and heat exchange efficiency. It is particularly preferable to use a metal-made bellows tube in a corrugated form having a multiplicity of repetitive concavo-convex nearly orthogonal to the axis of the heat exchange element 54.

The heat exchanger housing 5, the heating medium chamber-forming member 55 and the partitioning wall 56 can be made of various materials, for example, polyolefin such as polyethylene or polypropylene, an ester resin (e.g. polyester such as polyethylene terephthalate, or polybutylene terephthalate), a styrene resin (e.g. polystyrene, MS resin or MBS resin), a resin material such as polycarbonate, various kinds of ceramics materials or a metal material.

With reference to FIGS. 1-3, the following is a description of the flow of heating medium in the heat exchanging part 1B of the oxygenator 1.

The heating medium entering through the heating medium inlet port 52, first flows to the inlet heating medium chamber 57 and then to the outer peripheral side of the heating medium forming member 55 via the opening 59*a*, thus spreading over the entire periphery of the heating medium forming member 55 and going into the multiplicity of recesses of the bellows (to the inside of hollow annular projections) of the heat exchange element 54. This heats up or cools down the heat exchange element 54 that is in contact with the heating medium. Thus, heat exchange (heating or cooling) is effected with the blood flowing at the outer peripheral side of the heat exchange element 54.

The heating medium serving to heat or cool the heat exchange element 54 enters the outlet heating medium chamber 58 through the opening 59*b* and then exits at the heating medium outlet port 53.

Although the oxygenator described above and illustrated in the drawing figures includes the heat exchanging part 1B, it is to be understood that the heat exchanger part 1B is not required, and the oxygenator part 1A can be used independently of the heat exchanger part 1B.

Referring to FIGS. 1-4, the following describes the blood flow in the oxygenator 1 of this embodiment.

The blood enters at the blood inlet port 51 and flows into the blood chamber 50, i.e., between the inner surface of the heat exchanger housing 5 and the heat exchange element 54, where the blood contacts the outer surface of the plurality of hollow annular projections of the heat exchange element 54, thus effecting heat exchange (heating or cooling). The blood thus subjected to heat exchange gathers at a downstream side of the blood chamber 50 and then flows into the housing 2 of the oxygenating part 1A through the blood inlet aperture 24.

The blood passing through the blood inlet aperture 24 flows downstream along the blood passage 33. Meanwhile, the gas (gas containing oxygen) supplied through the gas inlet port 26 is distributed by the gas inlet chamber 261 into the gas passages 32, i.e., the lumens of the hollow fiber membranes 31. After passing along the gas passages 32, the gas is collected in the gas outlet chamber 271 and allowed to exit at the gas outlet port 27. The blood, flowing along the blood passage 33 contacts the outer surfaces of the hollow fiber membranes 31 so that gas exchange (oxygenation or carbon dioxide removal) takes place with the gas flowing through the gas passages 32.

If bubbles are present in the gas-exchanged blood, the bubbles are caught by the filter member 41. The bubbles (bubble gas), caught at the filter member 41, enter the lumens (gas passages 422) of the hollow fiber membranes 421 via the multiplicity of fine pores in the walls of the hollow fiber membranes 421 of the gas outlet hollow fiber membrane layer 42 located adjacent to and upstream of the filter member 41. The bubble gas entering the hollow fiber membranes 421 is discharged at the gas outlet port 29 through the small space 233.

The blood thus subjected to gas exchange and bubble removal flows out of the blood outlet port 28.

In the oxygenator 1 of this embodiment, it is preferable that surfaces to be contacted with blood (e.g., the inner surface of the housing 2, the inner surface of the heat exchanger housing 5, the surface of the heating medium chamber-forming member 55, the surface of the partitioning wall 56, the setting member 7, and the surfaces of the partitioning walls 8, 9 facing the blood passage 33) are made antithrombotic. The antithrombotic surface can be formed by coating and fixing an antithrombotic material on the surface. Examples of the antithrombotic material include heparin, urokinase, HEMA-St-HEMA copolymer, poly-HEMA and so on.

The flow rate of blood through the blood inlet port 51 is not especially limited because it may be different depending upon, for example, the patient's physique and the operational scheme. However, usually, a blood flow rate of 0.1-2.0 L/min is preferred in the case of an infant or child, a blood flow rate of 2.0-5.0 L/min is preferred in the case of a child in elementary or middle school, and a blood flow rate of 3.0-7.0 L/min is preferred in the case of an adult.

The flow rate of the gas supplied through the gas inlet port 26 is also not particularly limited because it is different depending upon, for example, the patient's physique and the operational scheme. However, usually, a gas flow rate of 0.05-4.0 L/min is preferred in the case of an infant or child, a gas flow rate of 1.0-10.0 L/min is preferred in the case of a child in elementary or middle school, and a gas flow rate of 1.5-14.0 L/min is preferred in the case of an adult.

Similarly, the oxygen concentration of the gas supplied through the gas inlet port 26 is not especially limited because it may differ depending upon, for example, the metabolic amount of oxygen/carbon-dioxide gas of a patient under operation. However, an oxygen concentration of 40-100% can be used.

The maximum continuous operation time of the oxygenator 1 can vary depending upon the patient's condition and the operational scheme. However, a time of approximately 2-6 hours can be considered. The maximum continuous operation time of the oxygenator 1 may, rarely, amount to a time as long as nearly 10 hours.

Figure 5:
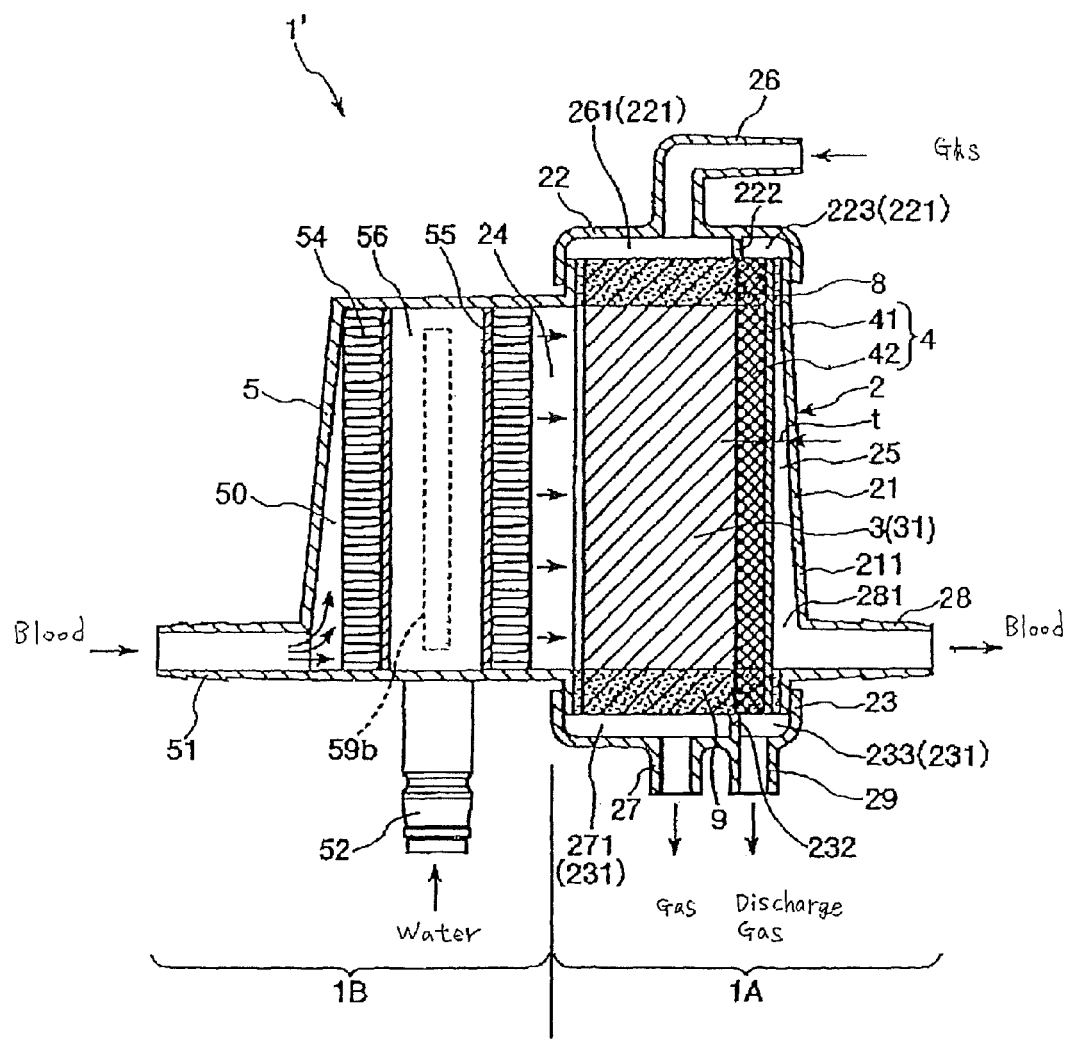
FIG. 5 is a cross-sectional side view of a second embodiment of an oxygenator.

FIG. 5 illustrates a second embodiment of the oxygenator. The description which follows primarily describes the differences between this embodiment and the foregoing embodiment described above. Thus, features of the oxygenator which are similar to those in the first embodiment are identified by the same reference numerals and a detailed description of such features is not repeated. This second embodiment is similar to the first embodiment, except for features relating to the housing.

In the oxygenator 1' shown in FIG. 5, the rectangular cylindrical housing body 21 (housing 2) has, at its downstream side, a wall (side wall) 211 inclined relative to the axis of the rectangular cylindrical housing body 21 (i.e., relative to the vertical). Thus, in the oxygenator 1', the rectangular cylindrical housing body 21 has a cross-sectional area gradually increasing toward the lower portion (toward a passage enlargement 281) in FIG. 5. Accordingly, between the inner surface (wall 211) of the rectangular cylindrical housing body 21 and the filter member 41, a gap is provided (i.e., a gap having a size or width t of a blood outlet aperture 25) that gradually increases toward the passage enlargement 281 (toward the downstream end).

By gradually increasing the gap size t, the blood moving down the blood outlet aperture 25 is decelerated until reaching the passage enlargement 281. By moderately decelerating the flow velocity, the blood is allowed to flow in a manner that does not significantly adversely affect a smooth flow, thus providing a flow-velocity distribution through the blood passage 33 with a result that the pressure loss of blood flow can be held relatively low.

Although FIG. 5 illustrates the gap size as increasing continuously and gradually, the wall 211 can be configured to provide a gap size t that increases stepwise toward the downstream end (i.e., toward the lower end).

The (lower) region of the blood outlet aperture 25 increasing in gap size t is due to an increasing cross-sectional area of the blood outlet aperture 25A, and hence is capable of exhibiting a function similar to that of an enlargement (e.g., the enlargement 282A in a further embodiment described below).

Figure 6:
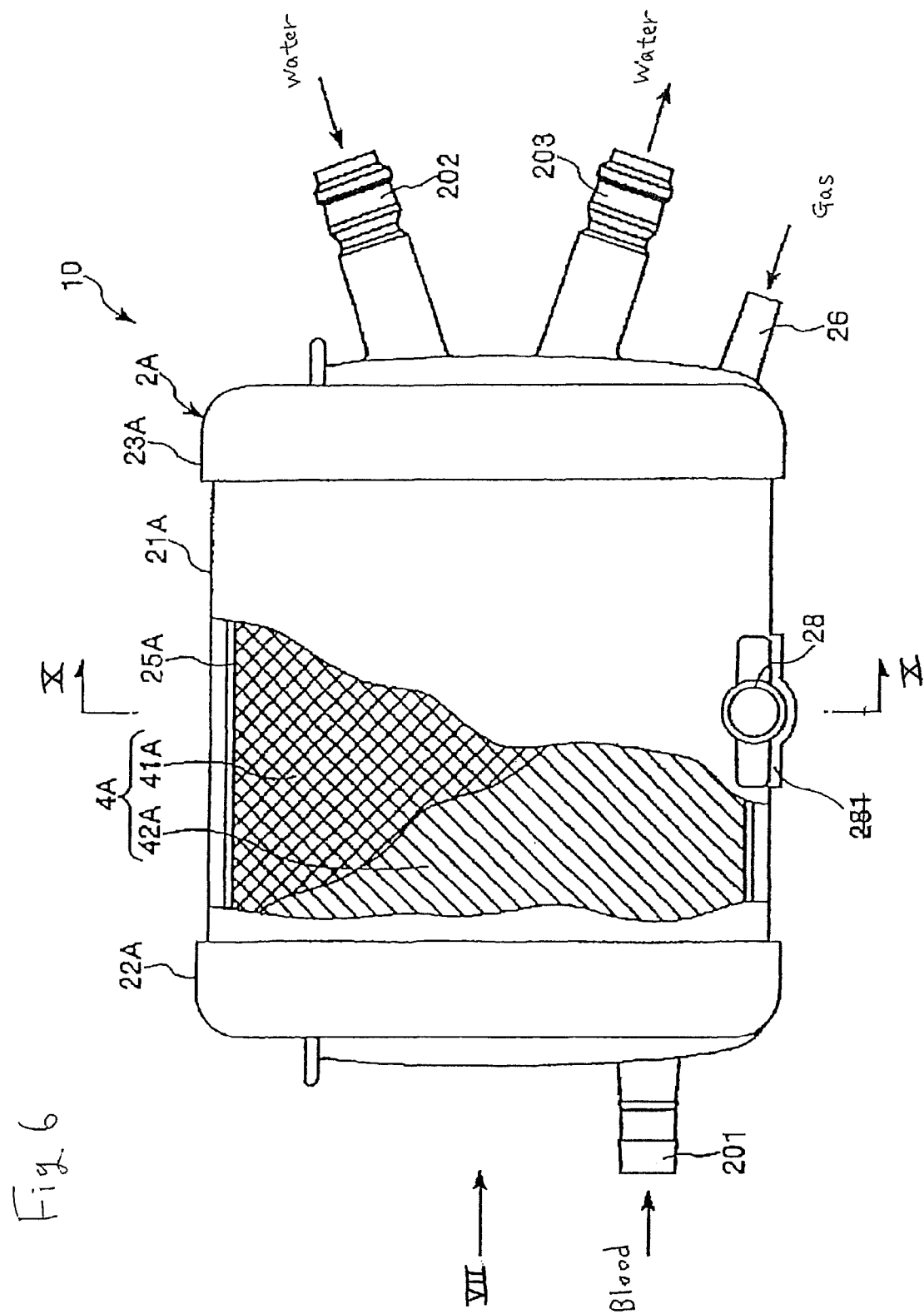
FIG. 6 is a plan view of a third embodiment of an oxygenator with a portion of the housing body removed.
Figure 7:
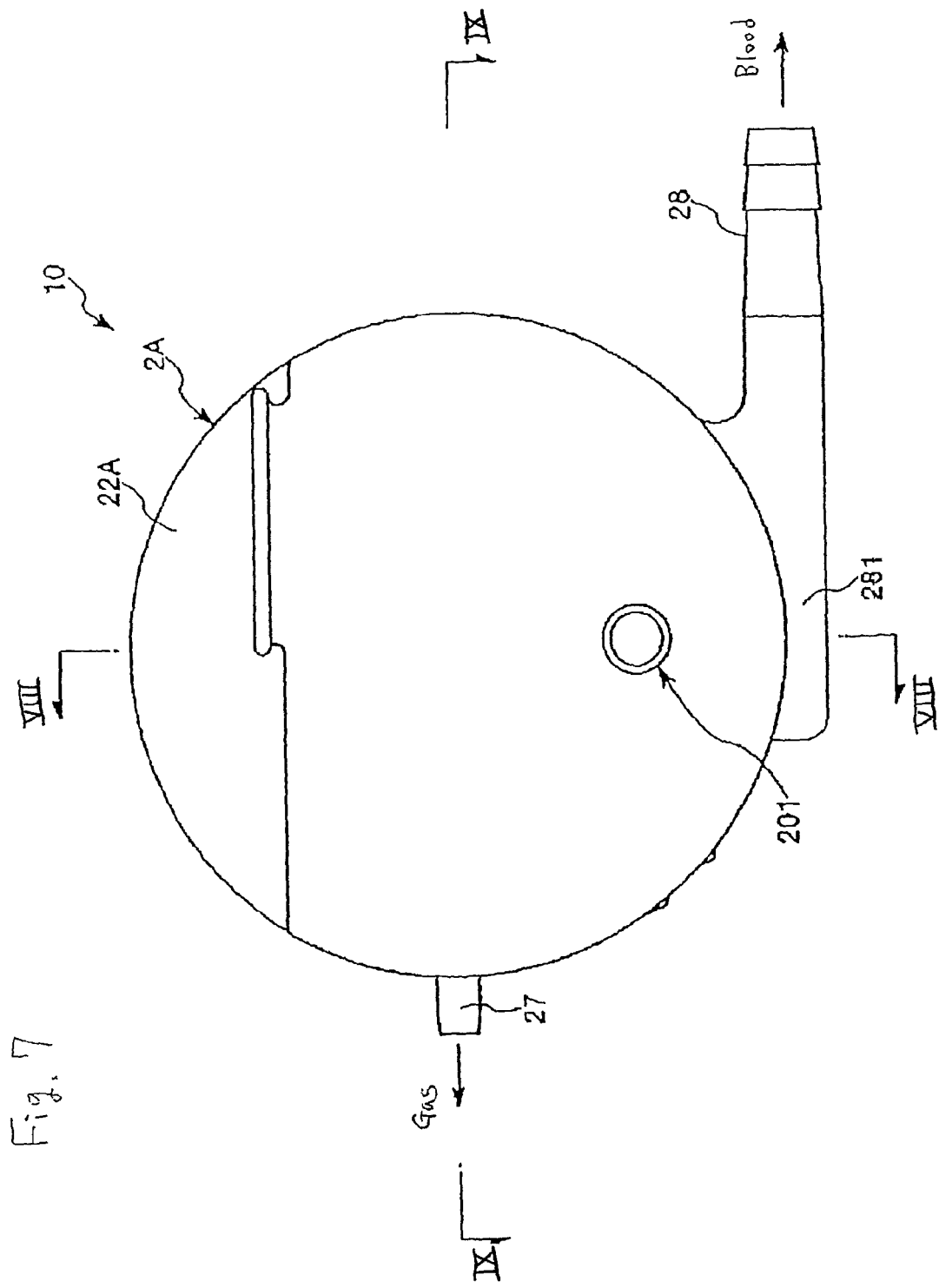
FIG. 7 is a left side or end view of the oxygenator shown in FIG. 6 as viewed along the arrow VII-VII in FIG. 6.
Figure 8:
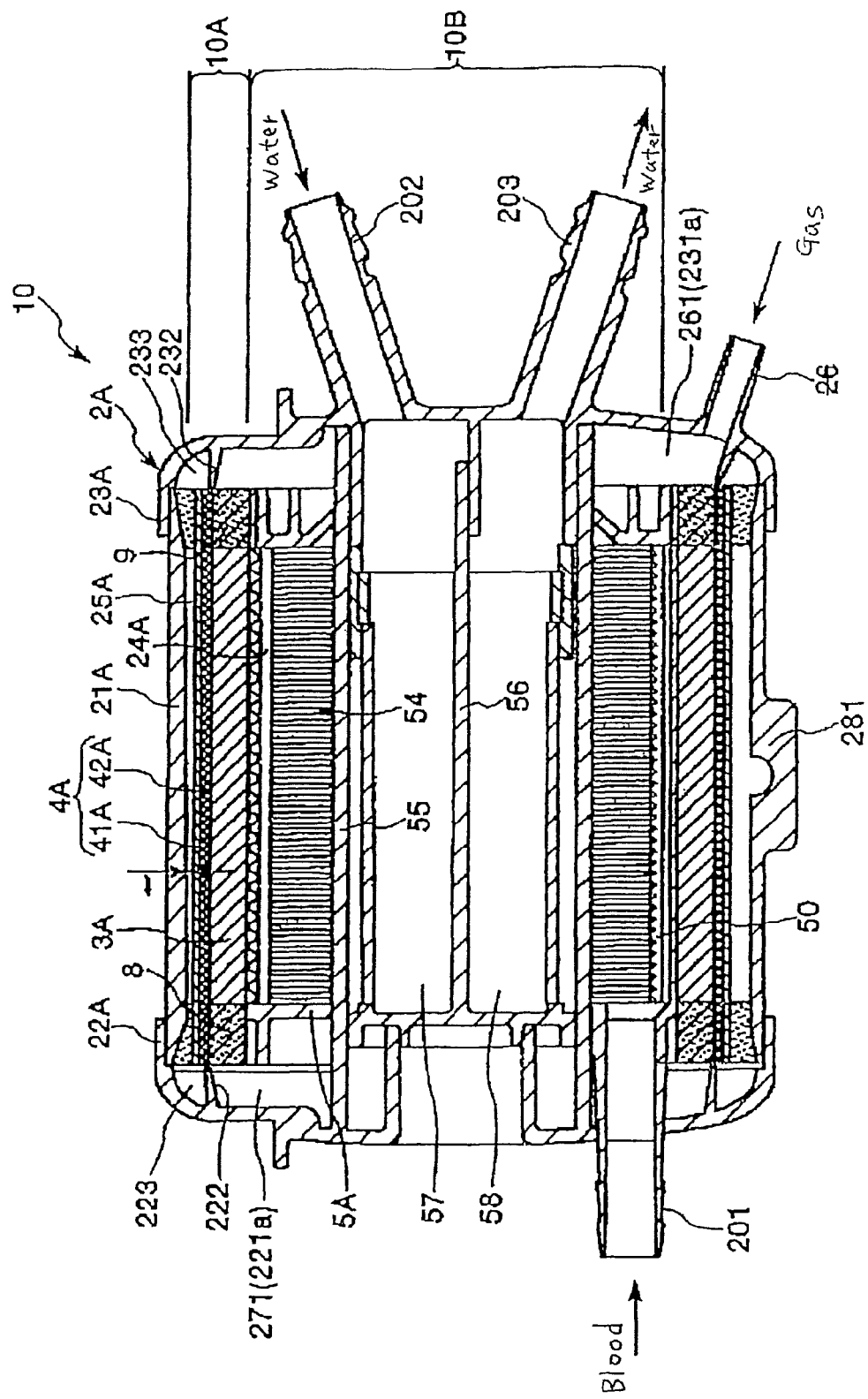
FIG. 8 is a cross-sectional view of the oxygenator shown in FIG. 7 taken along the section line VIII-VIII in FIG. 7.
Figure 9:
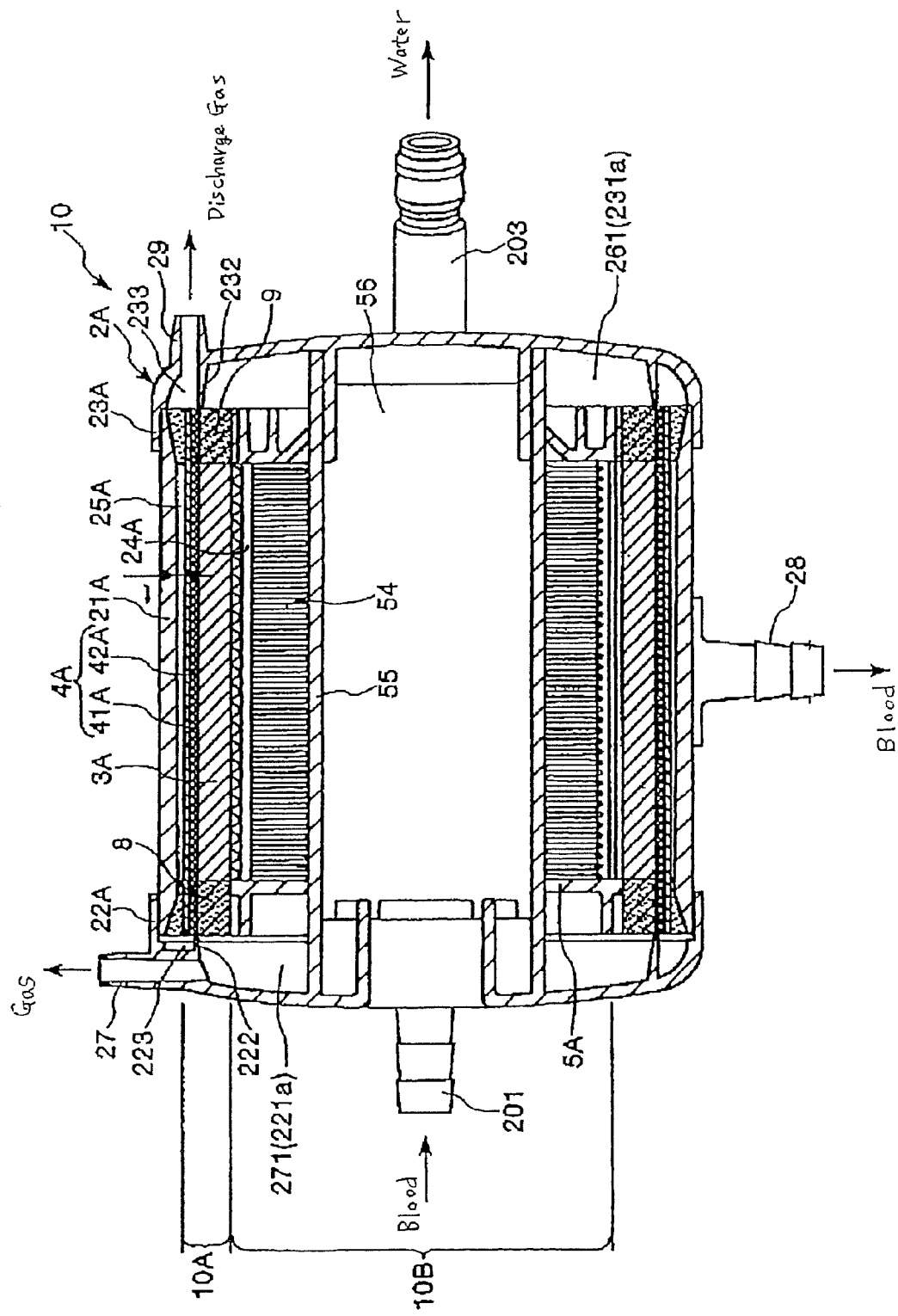
FIG. 9 is a cross-sectional view of the oxygenator taken along the section line IX-IX in FIG. 7.

FIGS. 6-11 illustrate a third embodiment of an oxygenator described herein. In FIGS. 6, 8 and 9, the left side is referred to as "left" or "leftward" while the right side is referred to as "right" or "rightward". In FIGS. 6-8, 10 and 11, the upper side is referred to as "upper" or "above" while the lower side is referred to as "lower" or "below". In FIGS. 6-11, the interior of the oxygenator is referred to as the "blood inlet side" or "upstream side" while the exterior thereof is referred to as "blood outlet side" or "downstream side".

The description which follows primarily describes the differences between this embodiment and the foregoing embodiments described above. Thus, features of the oxygenator which are similar to those previously described in other embodiments are identified by the same reference numerals and a detailed description of such features is not repeated.

This third embodiment is similar to the first embodiment except that the oxygenator is different in its overall shape. The oxygenator 10 in the illustrated embodiment possesses a nearly cylindrical form in its entire or overall shape (exterior shape). The oxygenator 10 is a heat exchanger-equipped oxygenator including a heat exchanging part (heat exchanger) 10B provided in the interior thereof which is nearly similar in structure to the heat exchanging part 1B of the first embodiment, and an oxygenating part 10A provided at an outer periphery of the heat exchanging part 10B for performing gas exchange with respect to the blood.

Figure 10:
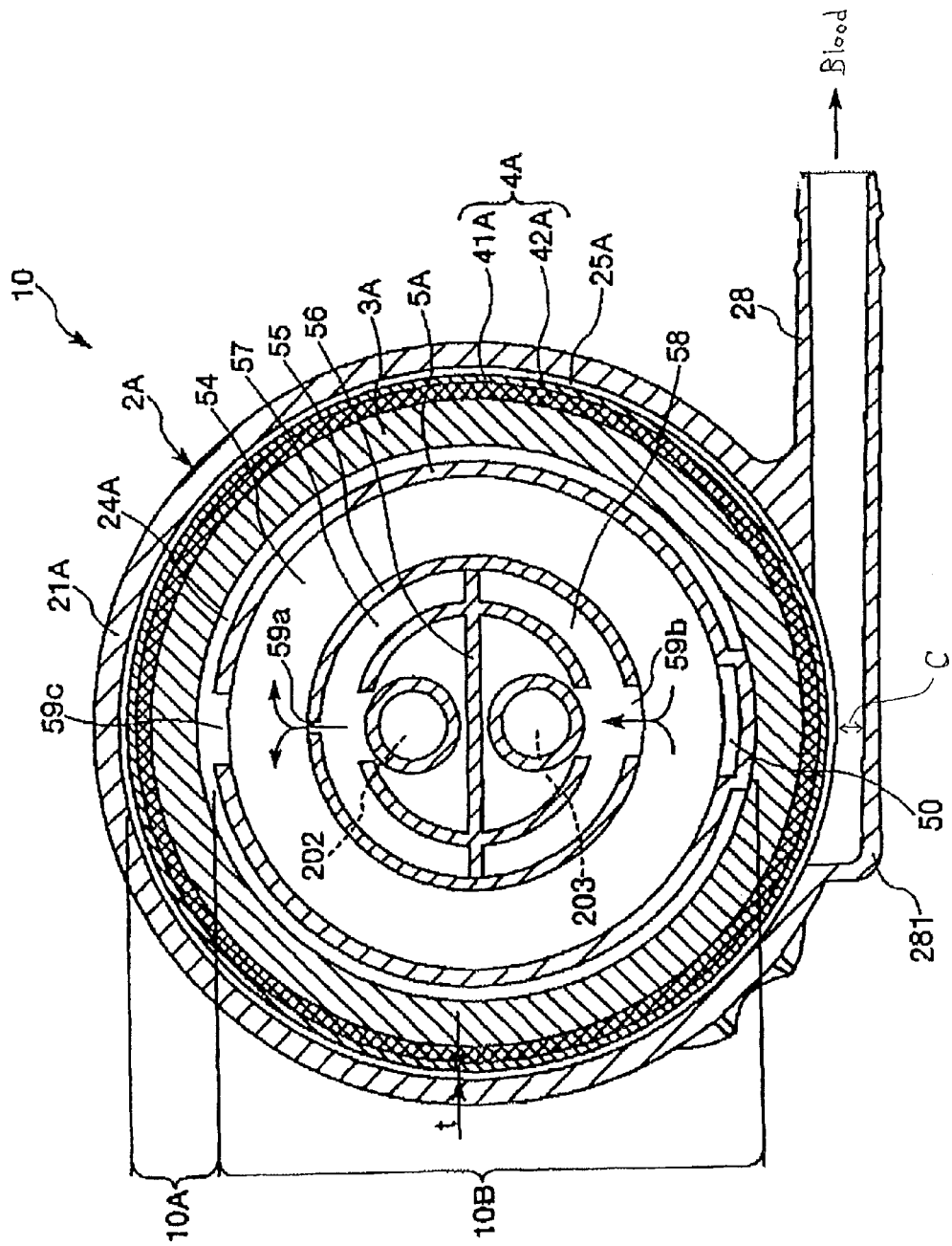
FIG. 10 is a cross-sectional view taken along the section line X-X in FIG. 6.

The oxygenator 10 comprises a housing 2A in which is received or positioned the oxygenating part 10A and the heat exchanging part 10B. As shown in FIG. 10, the oxygenating part 10A and the heat exchanging part 10B are arranged concentric to the housing 2A.

The heat exchanging part 10B is further received in a heat exchanger housing 5A within the housing 2A. By virtue of the heat exchanger housing 5A, both ends of the heat exchanging part 10B are fixed relative to the housing 2A.

The housing 2A is comprise of a housing body 21A possessing a cylindrical form (hereinafter referred to as a "cylindrical housing body"), a first header (upper lid) 22A in a dish form closing the left-side aperture or opening of the cylindrical housing body (barrel) 21A, and a second header (lower lid) 23A in a dish form closing the right-side aperture or opening of the cylindrical housing body 21A.

The cylindrical housing body 21A, the first header 22A and the second header 23A are each formed of, for example, polyolefin such as polyethylene or polypropylene, an ester resin (e.g. polyester such as polyethylene terephthalate, or polybutylene terephthalate), a styrene resin (e.g. polystyrene, MS resin or MBS resin), a resin material such as polycarbonate, a ceramics material in various kind or a metal material. The first header 22A and the second header 23A are secured in a liquid-tight manner to the cylindrical housing body 21A by joining, for example by fusion or an adhesive.

A tubular blood outlet port 28 is formed in the outer periphery of the cylindrical housing body 21A. The blood outlet port 28 projects nearly in a tangential direction to the outer peripheral surface (circumference) of the cylindrical housing body 21A as shown in FIGS. 7 and 10. In the construction shown in FIG. 10, the portion of the blood outlet port 28 which opens to the housing body 21A is offset outwardly away from the inner peripheral surface of the cylindrical housing body 21A (an imaginary continuation of the inner peripheral surface) by a distance C to thus provide a passage enlargement as described in more detail below. By way of example, the distance or offset C can preferably be approximately 0.5-4 mm.

A blood outlet aperture 25A, described in more detail below, is in a cylindrical form concentric to the cylindrical housing body 21A. The blood outlet port 28 thus projects nearly tangentially to the circumference of the blood outlet aperture 25A. This allows the blood pass along the blood outlet aperture 25A to flow into the blood outlet port 28 relatively smoothly and easily.

A passage enlargement 281, possessing a box form (or a groove form), is provided in a region nearby the blood outlet port 28 and close to the cylindrical housing body 21A or housing 2 (at and around the upstream end), i.e., in a base region of the blood outlet port 28. The blood outlet port 28 has a lumen in communication with a lumen of the passage enlargement 281, thus forming a passage through which the blood passing through a filter member 41A, described in more detail below, is to pass. As shown in FIGS. 8 and 10, the passage enlargement 281 is provided as a region where the passage is increased in its cross-sectional area.

In the oxygenator 1, the blood passing through the filter member 41A, upon entering the passage enlargement 281, is decelerated at a rate reciprocal to the increasing ratio of the passage cross-sectional area. The blood whose velocity has been decelerated reaches the blood outlet port 28.

A blood inlet port 201 and a gas outlet port 27 that are tubular in form project from the first header 22A. The blood inlet port 201 is formed in an end surface of the first header 22A such that the axis of the blood inlet port 201 is offset from the center of the first header 22A as shown in FIG. 7. The gas outlet port 27 is formed in the outer periphery of the first header 22A such that the axis of the gas outlet port 27 intersects the center of the first header 22A as shown in FIG. 7.

A gas inlet port 26, a gas outlet port 29, a heating medium inlet port 202 and a heating medium outlet port 203 that are tubular in form project from the second header 23A. The gas inlet port 26 and the gas outlet port 29 are formed in the end-surface of the second header 23A at an edge of the second header 23A. The heating medium inlet port 202 and the heating medium outlet port 203 are formed nearly centrally in the end surface of the second header 23A. The heating medium inlet port 202 and the heating medium outlet port 203 are somewhat inclined so that their axes form an angle relative to the centerline of the second header 23A.

The oxygenating part 10A is concentrically arranged or received in the interior of the housing 2A. The oxygenating part 10A is cylindrical in form and extends along the inner peripheral surface of the housing 2A as shown in FIGS. 8-10. The oxygenator 10A is comprised of a hollow fiber membrane bundle 3A in a cylindrical form, a filter member 41A serving as bubble removal means 4A provided on the outer peripheral side (blood outlet side) of the hollow fiber membrane bundle 3A, and gas outlet hollow fiber membrane layer 42A. The hollow fiber membrane bundle 3A, the gas outlet hollow fiber membrane layer 42A and the filter member 41A are arranged in that order, with the hollow fiber membrane bundle 3A being located innermost relative to the gas outlet hollow fiber membrane layer 42A and the filter member 41A.

Figure 11:
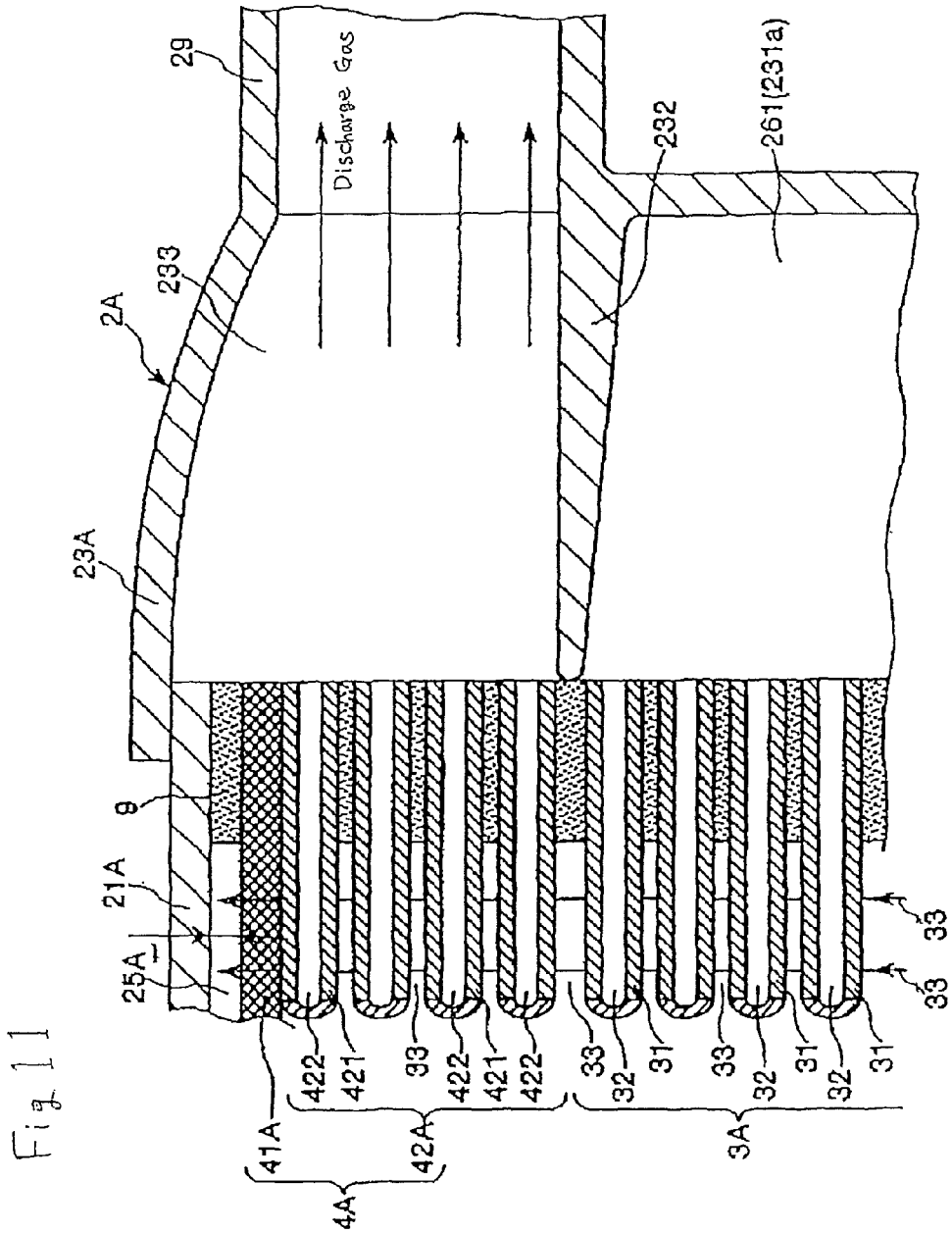
FIG. 11 is an enlarged cross-sectional view of an upper right region (fixing region of a hollow fiber membrane bundle, filter member and gas outlet hollow fiber membrane layer) in FIG. 9.

As shown in FIG. 11, the hollow fiber membrane bundle 3A is formed by integrating a multiplicity of hollow fiber membranes 31 serving for gas exchange.

The arrangement pattern, direction, etc. of the hollow fiber membranes 31 of the hollow fiber membrane bundle 3A can be arranged vertical relative to the axis of the housing 2A, or can be arranged to form a structure in which the hollow fiber membranes 31 have obliquely intersecting points (intersections) with another (intersections), a structure in which all or part of the hollow fiber membranes 31 are arranged curved, or a structure in which all or part of the hollow fiber membranes 31 are arranged in a corrugated, helical, spiral or annular manner.

The hollow fiber membranes 31 at their opposite ends (left and right ends) are fixed to the inner surfaces of the rectangular cylindrical housing body 21A by partitioning walls 8, 9 as shown in FIGS. 9 and 10.

The hollow fiber membrane bundle 3A is charged nearly fully between the cylindrical housing body 21A and the heat exchanger part 10B. Due to this, the hollow fiber membrane bundle 3A is wholly placed nearly in a cylindrical form. This provides a relatively high charge efficiency of the hollow fiber membranes 31 (with less dead space) in the cylindrical housing body 21A, thus contributing to a size reduction and performance improvement of the oxygenating part 10A.

The hollow fiber membranes 31, between the partitioning walls 8, 9 in the housing 2A, are exposed so that a blood passage 33 is formed outside the hollow fiber membranes 31, i.e., at the gaps between the hollow fiber membranes 31, allowing blood to flow from left to right in FIG. 2. The same is true for the hollow fiber membranes 421 of the gas outlet fiber membrane layer 42A.

A cylindrical blood inlet aperture (blood inlet space) 24A is formed as a blood inlet portion for the blood entering from the blood inlet port 201 upstream of the blood passage 33 (closer to the upstream surface of the hollow fiber membrane bundle 3A), i.e., between the oxygenator part 10A and the heat exchanging part 10B.

The blood entering the blood inlet aperture 24A flows in a direction peripheral of and lengthwise of the blood inlet aperture 24A and is thus allowed to flow to the entirety of the blood inlet aperture 24A. This makes it possible to efficiently transfer the blood from the heat exchanging part 10B to the oxygenating part 10A.

Downstream of the blood passage 33 (closer to the downstream surface of the hollow fiber membrane bundle 3A), a cylindrical gap is formed between the outer peripheral surface of the filter member 41A and the inner peripheral surface of the cylindrical housing body 21A. The gap is located where the blood which has passed through the filter member 41A is to flow, thus forming a blood outlet aperture (blood outlet space) 25A. A blood outlet portion is constituted by the blood exit aperture 25A, the passage enlargement 281 and the blood outlet port 28 communicating with the blood outlet aperture 25A through the passage enlargement 281. The blood outlet aperture 25A has a gap size t that is constant and extends circumferentially of the blood outlet aperture 25A.

The blood outlet aperture 25A thus arranged provides the blood exit portion with a space where the blood which has passed through the filter member 41A is to flow toward the blood outlet port 28. Thus, the blood can be discharged smoothly.

Between the blood inlet aperture 24A and the blood outlet aperture 25A, there exist the hollow fiber membrane bundle 3A, the filter member 41A, the gas outlet hollow fiber membrane layer 42A and the blood passage 33.

The thickness of the hollow fiber membrane bundle 3A (i.e., the radial length in FIG. 10) is not particularly limited, but is preferably approximately 2-100 mm, more preferably approximately 3-30 mm.

As mentioned before, the bubble removal means 4A is positioned downstream (closer to the blood exit portion) of the hollow fiber membrane bundle 3A, serving to catch bubbles in the blood and discharge the caught bubbles to the outside of the blood passage. The bubble removal means 4A comprises the filter member 41A and the gas outlet hollow fiber membrane layer 42A arranged upstream of the filter member 41A.

The filter member 41A is formed by a sheet member that is nearly rectangular in form (hereinafter also referred to as a "sheet"), wherein the sheet is wound in a cylindrical form. The filter member 41A has both ends respectively secured by the partitioning walls 8, 9 so that the filter member 41A is fixed in the housing 2A as shown in FIGS. 8 and 9.

The inner peripheral surface of the filter member 41A contacts the downstream surface (closer to the blood outlet portion) of the gas outlet hollow fiber membrane layer 42A. In the illustrated embodiment, the filter member 41A contacts and covers the entire outer surface of the gas outlet hollow fiber membrane layer 42A (inclusive of substantially the entire outer surface of the gas outlet hollow fiber membrane layer 42A). By thus providing the filter member 41A, the filter member 41A can be increased in effective area thus relatively fully exhibiting the capability of catching bubbles. By increasing the effective area of the filter member 41A, even if clogging occurs in a part of the filter member 41A (e.g., adhesion of blood aggregations), it is possible to suppress or prevent the possibility that blood flow through the filter member 41A will be entirely blocked.

The filter member 41A can be in a form similar to the filter member of the first embodiment, i.e., a mesh (meshwork) form, a woven fabric, a non-woven fabric or a combination thereof. Also, the material forming the filter member 41A can be similar to that of the filter member 41 of the first embodiment.

By arranging the filter member 41A thus structured, even if bobbles exist in the blood flowing along the blood passage 33, the bubbles can be caught to prevent bubbles from passing out of the blood outlet port 28.

The bubbles caught by the filter member 41A are removed by the gas outlet hollow fiber membrane layer 42A located upstream of the filter member 41A.

It is to be understood that the gas outlet hollow fiber membrane layer 42A described above is not essential and can be omitted, if desired. In embodiments where the gas outlet hollow fiber membrane layer 42A is not utilized, bubbles trapped by the filter member 41A are removed by the hollow fiber membranes 31.

That is, in the case that bubbles exist in the gas-exchanged blood, such bubbles are caught by the filter member 41A. The bubbles (bubble gas), caught at the filter member 41A pass through the multiplicity of fine pores of the hollow fiber membranes 31 of the hollow fiber membrane bundle 3 located upstream of the filter member 41A, and then enter the lumens of the hollow fiber membranes 31 (gas passages 32). The bubble gas entering the hollow fiber membranes 31 is discharged at the gas outlet port 27 through the gas outlet chamber 271.

As shown in FIG. 11, almost all of the hollow fiber membranes 421 forming the gas outlet hollow fiber membrane layer 42A are arranged nearly parallel with the hollow fiber membranes 31 forming the hollow fiber membrane bundle 3A. Both ends (i.e., the upper and lower ends) of the hollow fiber membranes 421 are respectively fixed to the inner surfaces of the cylindrical housing body 21A through the partitioning walls 8, 9 in a manner similar to the hollow fiber membranes 31 as shown in FIGS. 8 and 9.

The arrangement pattern, direction, etc. of the hollow fiber membranes 421 in the gas outlet hollow fiber membrane layer 42A are not limited to those mentioned as the gas outlet hollow fiber membrane layer 42A can be arranged as a structure in which the hollow fiber membranes 421 are arranged vertical to the axis of the housing 2A, a structure in which the hollow fiber membranes 421 have obliquely intersecting points (intersections) of one with another, a structure in which all or part of the hollow fiber membranes 421 are arranged curved, or a structure in which all or part of the hollow fiber membranes 421 are arranged in a corrugated, helical, spiral or annular manner.

The thickness of the gas outlet hollow fiber membrane layer 42A (i.e., the radial length in FIG. 10) is not particularly limited, but is preferably, approximately 1-50 mm, more preferably approximately 1-30 mm.

As shown in FIG. 9, a first chamber 221a is defined by the first header 22A, the partition wall 8, the heat exchanger housing 5A of the heat exchanging part 10B, and the heating medium chamber-forming member 55. The first chamber 221a is divided by a partition 222 into a gas outlet chamber 271 located close to the hollow fiber membrane bundle 3A and a small space 223 located close to the gas outlet hollow fiber membrane layer 42A. The partition 222 is located at the boundary between the hollow fiber membrane bundle 3A and the gas outlet hollow fiber membrane layer 42A. The hollow fiber membranes 31 have left-end openings opening into and communicating with the gas outlet chamber 271.

In addition, a second chamber 231a is defined by the second header 23A, the partition wall 9, the heat exchanger housing 5A of the heat exchanging part 10B, and the heating medium chamber-forming member 55. The second chamber 231a is divided by a partition 232 into a gas inlet chamber 261 located closer to the hollow fiber membrane bundle 3A and a small space 233 located closer to the gas outlet hollow fiber membrane layer 42A. The partition 232 is located at the boundary between the hollow fiber membrane bundle 3A and the gas outlet hollow fiber membrane layer 42A. The hollow fiber membranes 31 have right-end openings that open into and communicate with the gas inlet chamber 261 as shown in FIG. 11.

The hollow fiber membranes 31 each have a lumen forming a gas passage 32 through which gas is adapted to flow. The gas inlet port 26 and the gas inlet chamber 261 constitute a gas inlet located upstream of the gas passages 32, while the gas outlet port 27 and the gas outlet chamber 271 constitute a gas outlet portion located downstream of the gas passages 32.

The hollow fiber membranes 421 each have lumen forming a gas passage 422 through which the bubble gas, passing through a multiplicity of fine pores formed in the wall of the hollow fiber membrane 421, is adapted to flow.

The gas passages 422 (hollow fiber membranes 421) have left-end openings that open into and communicate with the small space 223. This allows the small space 223 to serve as a bubble reservoir for temporarily storing the bubble gas flowing out of the gas passages 422.

The gas passages 422 also have right-end openings that open into and communicate with the small space 233 as shown in FIG. 11. The small space 233 communicates with the gas outlet port 29.

With this structure, the bubble gas passing out of the right-end openings of the gas passages 422 enters the small space 233 and then the gas outlet port 29, thus being positively discharged out of the oxygenator 10 (housing 2A). This can positively prevent the bubbles in the blood flowing along the blood passage 33 from being discharged out of the blood outlet.

The bubbles in the bubble-containing blood located upstream of the filter member 41A are caught by the filter member 41A. The blood passing through the filter member 41A and subjected to bubble removal flows toward the blood outlet port 28. By sufficiently decreasing the velocity of the blood entering the passage enlargement 281, the blood moving toward the blood outlet port 28 is prevented from entraining (against the venturi effect), across the filter member 41A, the bubbles that are caught by the filter member 41A. This can positively prevent the bubbles of the blood from being discharged out of the blood outlet port 28.

As mentioned before, the oxygenating part 10A is arranged in the heat exchanging part 10B. The heat exchanging part 10B is similar in construction to the heat exchanging part 1B described above and so a detailed description is not repeated.

By thus arranging the heat exchanging part 10B in the oxygenating part 10A, a number of advantages can be realized. For example, the oxygenating part 10A and the heat exchanging part 10B are efficiently received in the same housing 2A and so there is less dead space. Gas exchange can thus be achieved efficiently by the relatively small-sized oxygenator 10. Additionally, because the oxygenating part 10A and the heat exchanging part 10B are placed in a closer arrangement than those in the first embodiment, the blood heat exchanged at the heat exchanging part 10B is allowed to flow rapidly into the oxygenator 10A. This can minimize the charge amount of blood in the blood inlet aperture 24A (blood passage 33) communicating between the heat exchanging part 10B and the oxygenator 10A. Further, the blood subjected top heat exchange at the heat exchanging part 10B can flow to the oxygenating part 10A rapidly without significant delay.

Referring to FIGS. 8-11, the following is a description of the blood flow in the oxygenator 10 of this embodiment.

In the oxygenator 10, the blood enters at the blood inlet port 201 and flows to the blood chamber 50, i.e., to between the inner peripheral surface of the heat exchanger housing 5A and the heat exchange element 54. The blood contacts the outer surface of the plurality of hollow annular projections forming the heat exchange element 54 to thus effect heat exchange (heating or cooling). The blood thus heat exchanged passes through an opening 59c formed in the upper portion of the heat exchanger housing 5A and the blood inlet opening 24A in that order, and then flows into the housing 2A of the oxygenator 10A.

The blood, passing through the blood inlet opening 24A flows downstream along the blood passage 33. Meanwhile, the gas supplied through the gas inlet port 26 (gas containing oxygen) is distributed from the gas inlet chamber 261 into the gas passages 32, i.e., into the lumens of the hollow fiber membranes 31. After flowing along the gas passages 32, the gas is collected in the gas outlet chamber 271 and is discharged at the gas outlet port 27. The blood flowing along the blood passage 33 contacts the outer surface of the hollow fiber membranes 31 where it is gas-exchanged (oxygenated, carbon dioxide removal) with the gas flowing through the gas passages 32.

If bubbles exist in the gas-exchanged blood, such bubbles are caught by the filter member 41A. The bubbles (bubble gas) caught at the filter member 41A pass through a multiplicity of fine pores of the hollow fiber membranes 421 of the gas outlet hollow fiber membrane layer 42A located adjacent and upstream of the filter member 41A, and then enters the lumens of the hollow fiber membranes 421 (gas passages 422). The bubble gas entering the hollow fiber membranes 421 is discharged at the gas outlet port 29 through the small space 233.

The blood, thus gas-exchanged and subjected to bubble removal, is allowed to exit at the blood outlet port 28.

Figure 12:
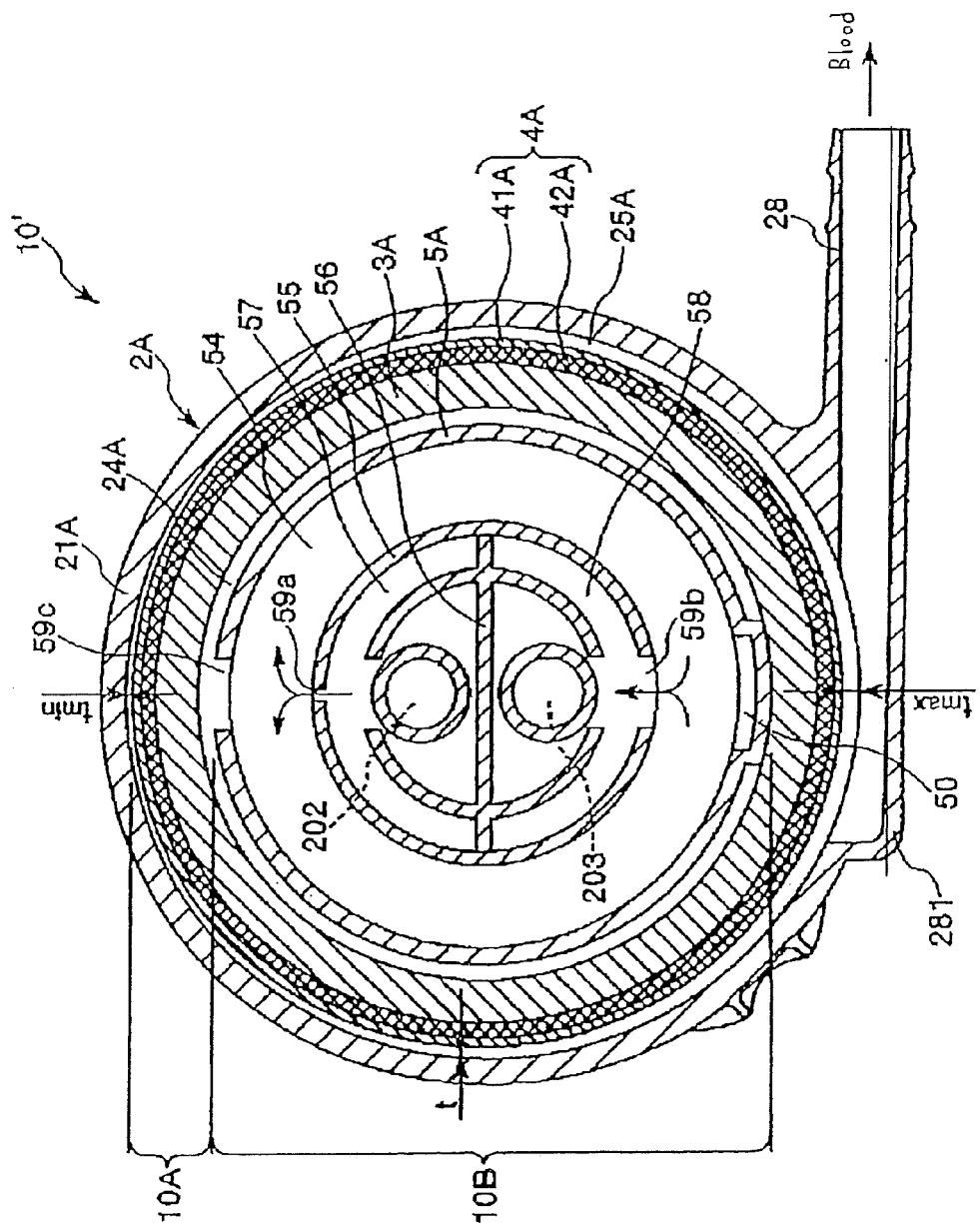
FIG. 12 is a cross-sectional view of a fourth embodiment of an oxygenator.

FIG. 12 illustrates a fourth embodiment of an oxygenator disclosed herein. The description which follows primarily describes the differences between this embodiment and the foregoing embodiments described above. Thus, features of the oxygenator which are similar to those previously described in other embodiments are identified by the same reference numerals and a detailed description of such features is not repeated.

The present embodiment is similar to the third embodiment described above, except that an oxygenating part is received or positioned eccentrically in the housing.

In the oxygenator 10' shown in FIG. 12, the oxygenator part 10A is arranged eccentric upward relative to the housing 2A (cylindrical housing body 21A). A gap exists between the inner peripheral surface of the cylindrical housing body 21A and the outer peripheral surface of the filter member 41A. This gap possesses a size (width dimension) t in the blood outlet aperture 25A, gradually increasing toward the downstream end along the periphery, i.e., toward the passage enlargement 281. Thus, in the blood outlet aperture 25A, the gap size t is a minimum size $t_{min}$ at its upper region (diametrically opposite to the passage enlargement 281) and is a maximum size $t_{max}$ at its lower region or downstream portion (i.e., at the passage enlargement 281).

Thus, the blood outlet aperture 25A, in a portion nearby the maximum gap $t_{max}$, is enlarged in its passage cross-sectional area, corresponding to a first enlargement 282A of a seventh embodiment described in more detail below, thus exhibiting a function similar to that of the first enlargement 282A.

By thus gradually increasing the gap size t, the blood passing through the blood outlet aperture 25A is further decelerated until reaching the passage enlargement 281. Owing to the moderate decrease of velocity, the blood is allowed to flow in a manner that does not significantly adversely affect a smooth flow, wherein the distribution of flow velocity is relatively uniform along the blood passage 33, with a result that the pressure loss due to blood flow can be suppressed.

Figure 13:
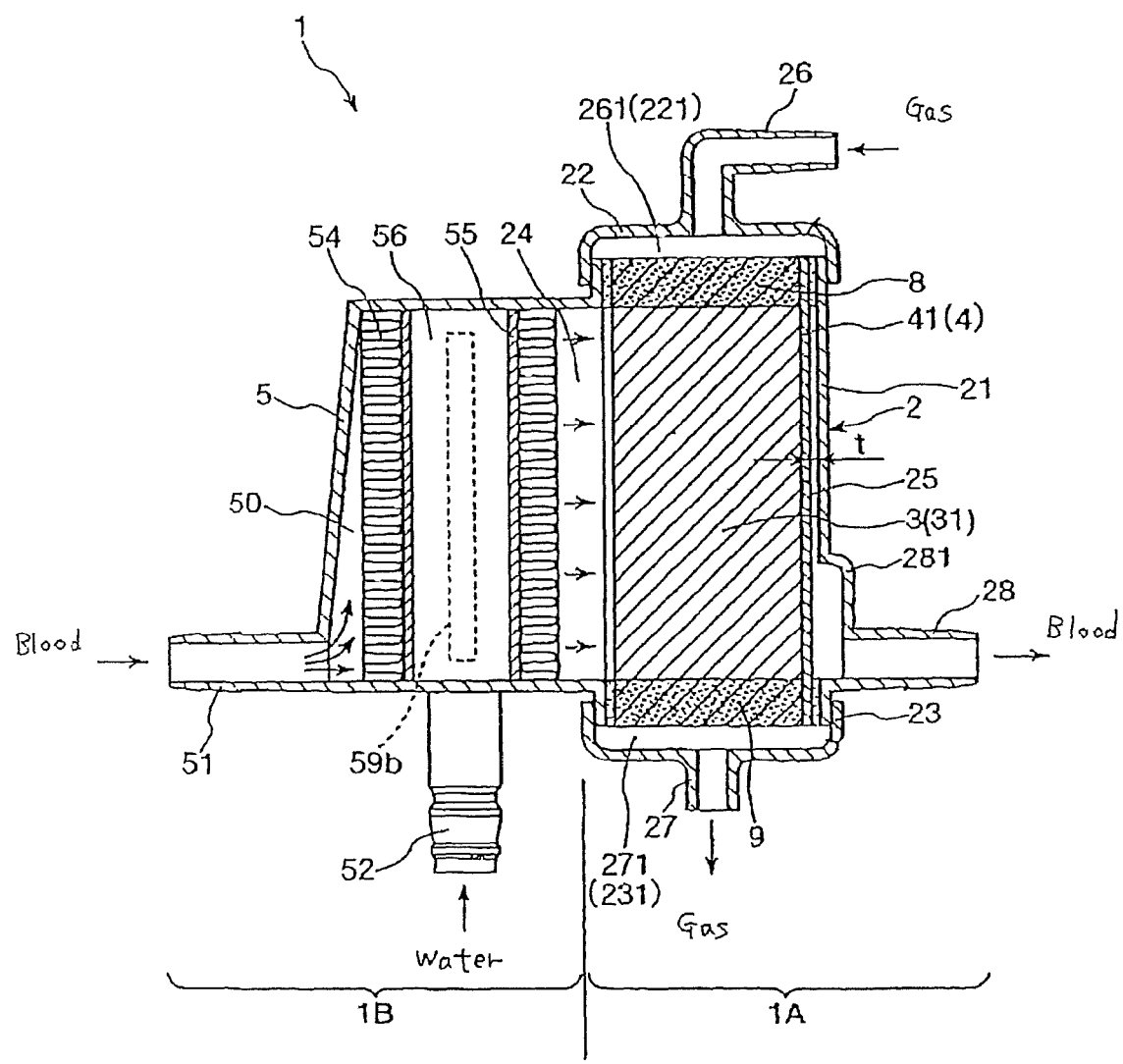
FIG. 13 is a cross-sectional side view of a fifth embodiment of an oxygenator.

FIG. 13 illustrates a fifth embodiment of an oxygenator. The following description primarily describes the differences between this embodiment and the first embodiment described above. Thus, features of the oxygenator which are similar to those previously described are identified by the same reference numerals and a detailed description of such features is not repeated.

The oxygenator 1 of this embodiment is similar to that of the first embodiment except that the gas outlet hollow fiber membrane layer 42 and the gas outlet port 29 are not present. That is, the bubble removal means 4 in this embodiment is comprised of the filter member 41. In addition, no partitions 222, 232 are provided because of the absence of the gas outlet port 29.

Figure 14:
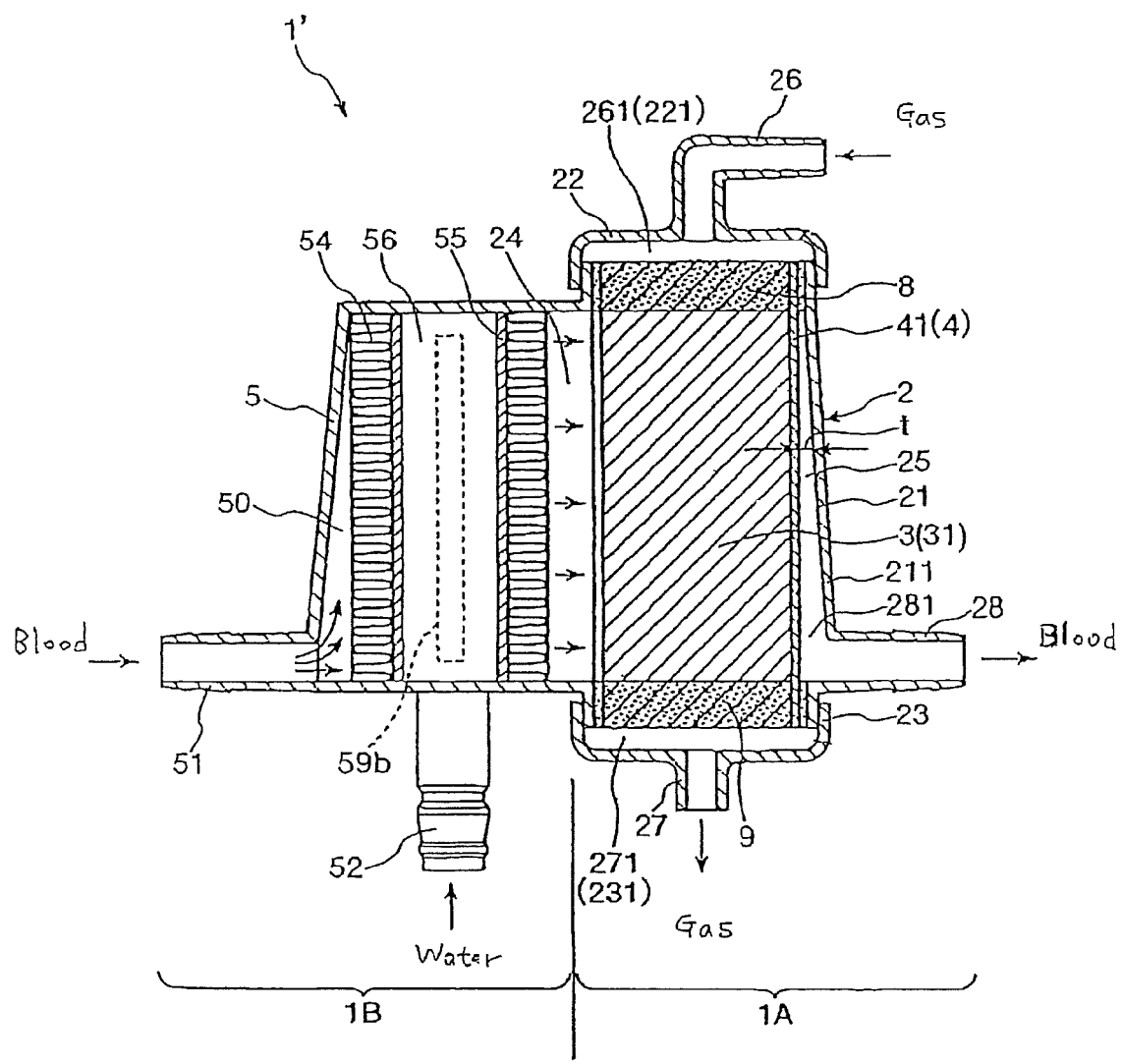
FIG. 14 is a cross-sectional side view of a sixth embodiment of an oxygenator.

FIG. 14 depicts a sixth embodiment of the oxygenator. The description which follows primarily describes the differences between this embodiment and the second embodiment described above. Thus, features of the oxygenator which are similar to those previously described are identified by the same reference numerals and a detailed description of such features is not repeated.

The oxygenator 1' according to this embodiment is similar to that of the second embodiment described above, except that the gas outlet hollow fiber membrane layer 42 and the gas outlet port 29 are not present. That is, the bubble removal means 4 used in this embodiment is comprised of the filter member 41. Also, no partitions 222, 232 are provided due to the absence of the gas outlet port 29.

Figure 15:
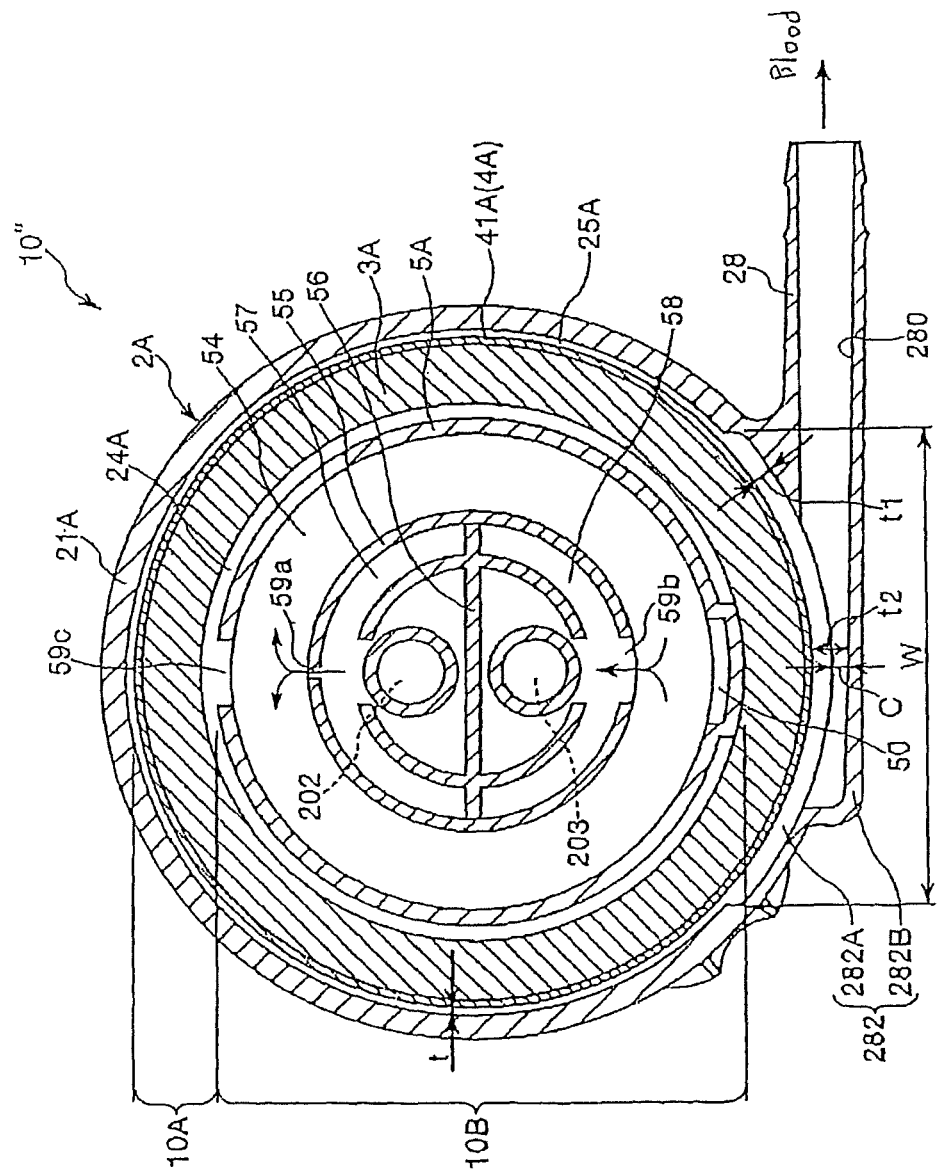
FIG. 15 is a cross-sectional view of a seventh embodiment of an oxygenator.
Figure 16:
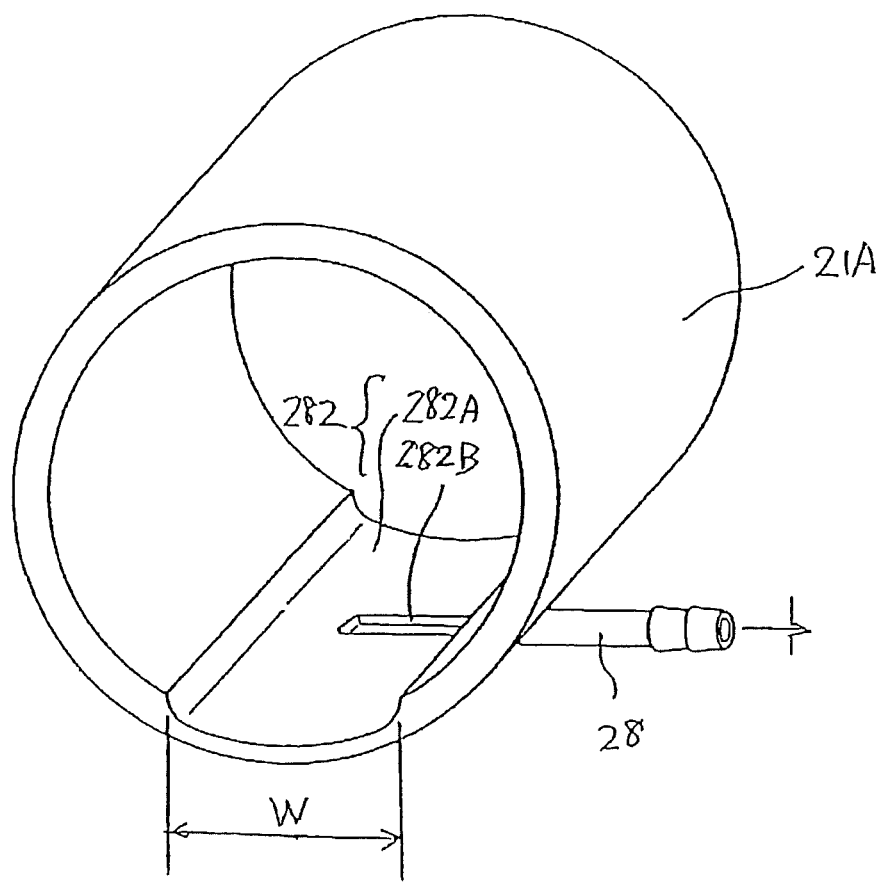
FIG. 16 is a perspective view of a cylindrical housing body of the oxygenator shown in FIG. 15.

FIGS. 15 and 16 illustrate a seventh embodiment of an oxygenator according to the invention. The following description primarily describes differences between this embodiment and the third embodiment described above. Thus, features of the oxygenator which are similar to those previously described are identified by the same reference numerals and a detailed description of such features is not repeated.

The oxygenator 10" of this embodiment is similar to that of the third embodiment shown in FIGS. 6-11, except that the gas outlet hollow fiber membrane layer 42, the gas outlet port 29 and the partitions 222, 232 are not present. In addition, the passage enlargement is different in structure.

The bubble removal means 4 in this embodiment is comprised of the filter member 41. As noted, the gas outlet hollow fiber membrane layer 42 and the gas outlet port 29 are not included. Also, no partitions 222, 232 are provided because of the nonexistence of a gas outlet port 29. The filter member 41 should preferably closely contact the hollow fiber membrane bundle 3A.

In this embodiment, a passage enlargement 282 is formed by a first enlargement 282A provided on an upstream side and a second enlargement 282B following the first enlargement 282A at a downstream side. This arrangement can help further prevent bubble from exiting out of the blood outlet port 28.

In the vicinity of the base of a blood outlet port 28, a groove (grooved recess) is formed axially along the inner peripheral surface of a cylindrical housing body 21A as best shown in FIG. 16. In the illustrated embodiment, the groove has a constant width. The groove constitutes the first enlargement 282A. In other words, the first enlargement 282A is provided as a portion of the cylindrical housing body 21A where the inner diameter of the housing body 21A is partially (locally) enlarged. The reason that the enlarged portion is preferably arranged along only a portion of the inner surface of the housing body 21A is to restrain increasing the priming volume while still reducing the blood current speed.

The groove, constituting the first enlargement 282A, is preferably formed throughout the axial (longitudinal) length of the cylindrical housing body 21A, i.e., over the entire axial extent of a blood outlet aperture 25A as shown in FIG. 16. This is because the blood can be decelerated uniformly and positively at axial points in the blood outlet aperture 25A.

By virtue of the first enlargement 282A structured in this way, the blood outlet aperture 25A has an increased gap size. That is, as compared to the first enlargement 282A not being present so that the gap size is represented by t, the gap size t1 (corresponding to $t_{max}$ of the fourth embodiment) where the first enlargement 282A is formed is greater than the foregoing gap size t. It is preferable that the relationship of t1/t is approximately 1.05-12, more preferably approximately 1.05-10. The relationship t1−t is preferably approximately 0.05-20 mm, more preferably approximately 0.1-10 mm.

When t1/t or t1−t is in the ranges mentioned above, a proper blood velocity decrease can be achieved by first enlargement 282A, thus contributing to improving the effect of preventing bubbles from exiting out of the blood outlet port 28.

The width (groove width) of the first enlargement 282A is not particularly limited. However, the first enlargement 282A has a width or chord length W (shown in FIG. 16) in its formed region as viewed laterally from the side where the blood outlet port 28 of the cylindrical housing body 21A is formed (i.e., as viewed from below in FIG. 15 and as viewed from the front in FIG. 16) that is preferably approximately 35-99% of the inner diameter of the cylindrical housing body 21A, more preferably approximately 45-75%. When the width W is within such numerical ranges, blood velocity decrease can be properly made by the first enlargement 282A, thus contributing to the effect of preventing bubble from exiting out of the blood outlet port 28.

The second enlargement 282B is similar to the passage enlargement 28 (passage enlargement 28 formed in the base of the blood outlet port 28) of the third embodiment.

In the oxygenator 10" of this embodiment, the blood passes the through the hollow fiber bundle 3A and the filter member 41A in that order and then enters the blood outlet aperture 25A. The blood flows in the blood outlet aperture 25A along its periphery and toward the first enlargement 282A, and flows into the first enlargement 282A where the blood passage increases its width from t to t1. Thus, the blood is decreased in flow velocity. The blood, entering the first enlargement 282A flows along the first enlargement 282A toward the lengthwise center thereof (toward the second enlargement 282B), and flows into the second enlargement 282B. Here again, the blood is decelerated. Then, the blood flows to the blood outlet port 28 and to the outside of the housing 2A.

The bubbles trapped by the filter member 41 enter into the inside lumen of the hollow fiber membranes of the hollow fiber membrane bundle 3A through the multiplicity of pores formed in the hollow fiber membranes located close to the filter member 41. The other embodiments (e.g., the fifth and sixth embodiments described above, and the eighth and ninth embodiments described below) have the same bubble removal mechanism as this seventh embodiment.

Figure 17:
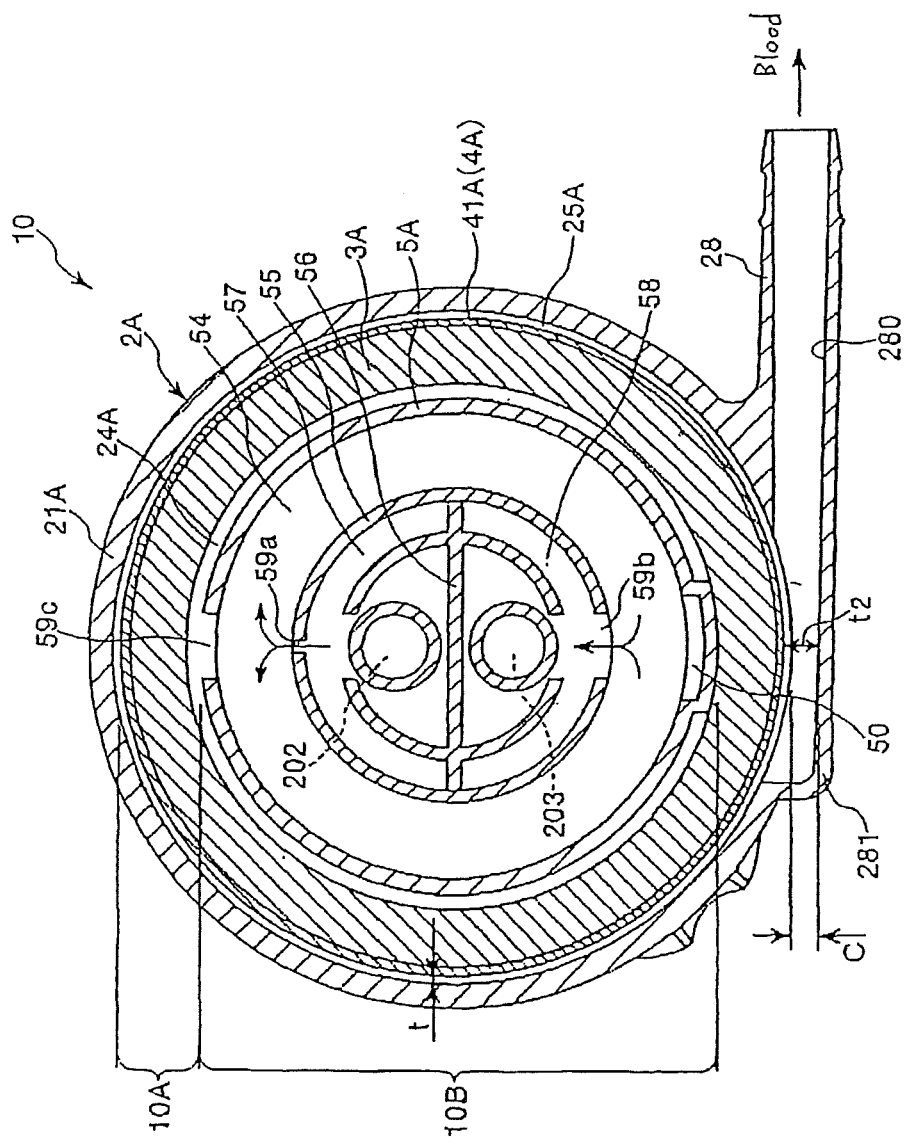
FIG. 17 is a cross-sectional view of an eighth embodiment of an oxygenator.

FIG. 17 illustrates an eighth embodiment of an oxygenator. The description which follows primarily describes the differences between this embodiment and the third embodiment described above. Thus, features of the oxygenator which have already been described are identified by the same reference numerals and a detailed description of such features is not repeated.

The oxygenator 1 of this embodiment is similar to that of the third embodiment, except that the gas outlet hollow fiber membrane layer 42A and the gas outlet port 29 are not present. That is, a filter member 41A is provided by contacting its inner peripheral surface with the downstream surface of the hollow fiber membrane bundle 3A (closer to the blood outlet). In this embodiment, the bubble removal means 4A is comprised of the filter member 41A.

In addition, this embodiment does not include the partitions 222, 232 because of the absence of the gas outlet port 29.

Figure 18:
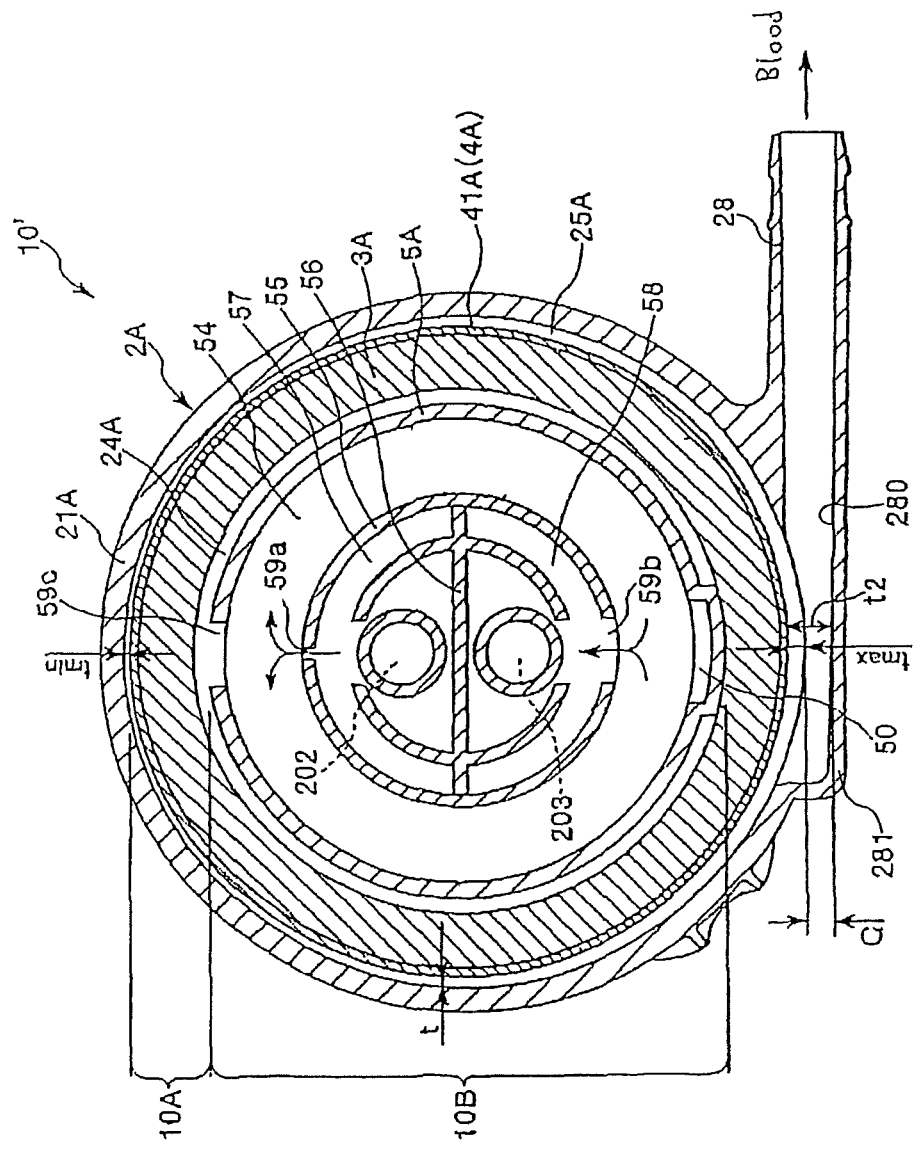
FIG. 18 is a cross-sectional view of a ninth embodiment of an oxygenator.

FIG. 18 depicts a ninth embodiment of an oxygenator. The description which follows primarily describes the differences between this embodiment and the fourth embodiment described above. Thus, features of the oxygenator which have already been described are identified by the same reference numerals and a detailed description of such features is not repeated.

The oxygenator 10 in this embodiment is similar to that of the fourth embodiment, except that the gas outlet hollow fiber membrane layer 42A and the gas outlet port 29 are not present. Namely, a filter member 41A is provided by contacting its inner peripheral surface with the outer surface of a hollow fiber membrane bundle 3A, including the downstream surface of the hollow fiber membrane bundle 3A (closer to the blood outlet portion). In this embodiment, the bubble removal means 4A is comprised of the filter member 41A.

This embodiment does not include the partitions 222, 232 because of the absence of the gas outlet port 29.

Figure 19:
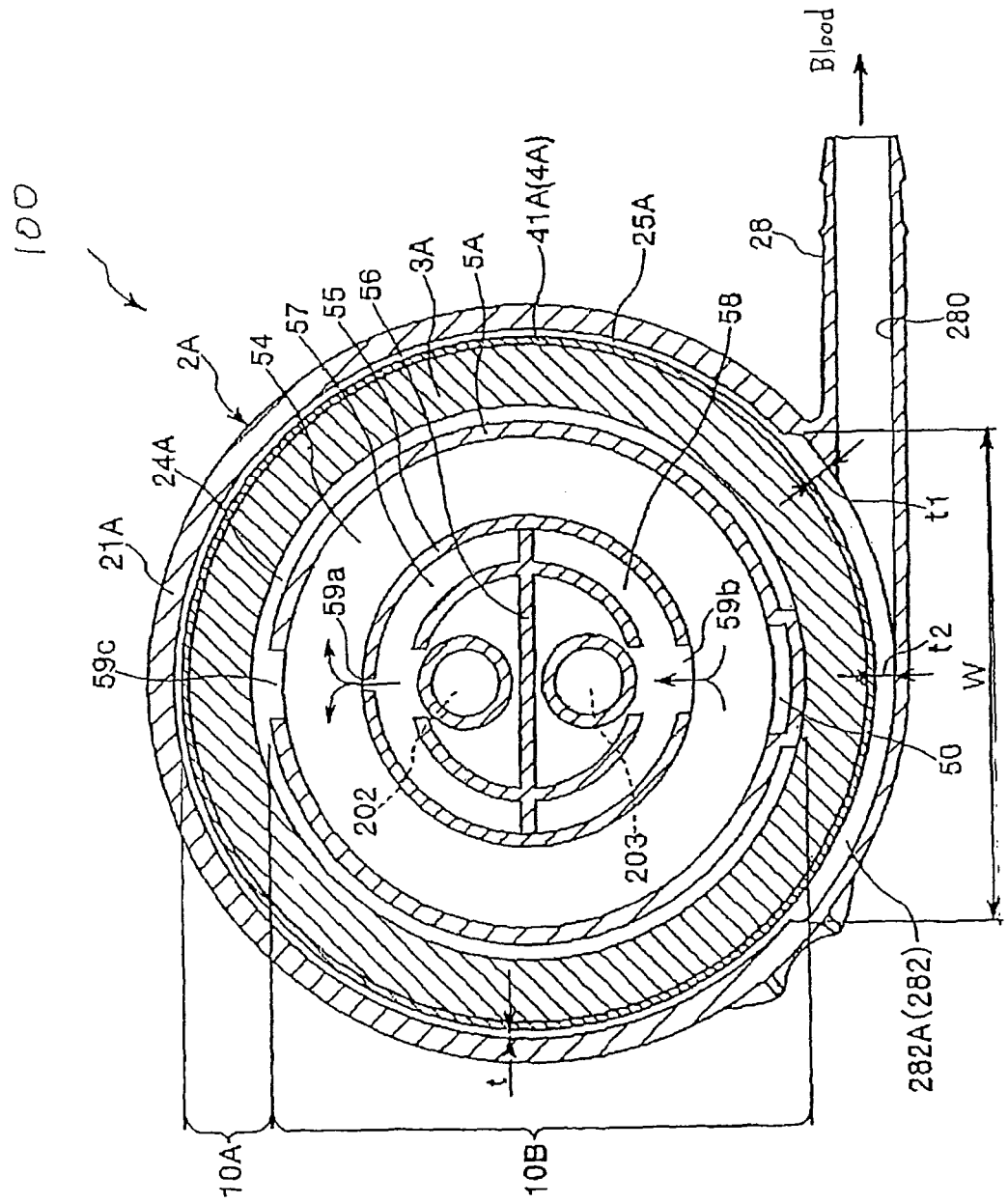
FIG. 19 is a cross-sectional view of a tenth embodiment of an oxygenator.

FIG. 19 is an illustration of a tenth embodiment of an oxygenator as disclosed herein. The description which follows primarily describes the differences between this embodiment and the seventh embodiment described above. Thus, features of the oxygenator which have already been described are identified by the same reference numerals and a detailed description of such features is not repeated.

The oxygenator 100 in this embodiment is similar to that of the seventh embodiment, except that instead of including both a first enlargement and a second enlargement as in the seventh embodiment, this tenth embodiment includes only the first enlargement.

The oxygenator has been described by way of the illustrated embodiments. However, the invention is not limited to such embodiments because various elements constituting the oxygenator can be replaced with features or elements capable of exhibiting the same or similar equivalent functions.

For example, different structures from those illustrated and described are appropriate for the structure or form of the housing, including the heat exchanger housing, and the position and projecting direction of the gas inlet port, gas outlet port, blood outlet port, blood inlet port, heating medium inlet port, heating medium outlet port, etc. The position of the oxygenator in use (positional relationship of various elements relative to the vertical direction) is also not limited to the illustrated position.

Below is a description of concrete examples of the oxygenator disclosed herein.

Example 1

Three types (models 1, 2 and 3) of oxygenators were fabricated according to the seventh embodiment shown in FIGS. 15 and 16, but differing from one another in the size of the cylindrical housing body (outer shell) and hollow fiber membrane bundle. The constructions are detailed in Table 1. The oxygenator has an outer shell formed with a second enlargement as a passage enlargement in a base of the blood outlet port as shown in FIG. 15, and a first enlargement in a groove form extending lengthwise of the outer shell in the vicinity of the second enlargement in the inner peripheral surface of the outer shell as shown in FIG. 16. The hollow fiber membranes used are those used in Capiox® RX25, RX15 and RX05 marketed by Terumo Kabushiki Kaisha. The hollow fiber membranes are wound around the core like the Capiox RX25, RX15 and RX05.

The filter member is made of a hydrophilic sheet-formed mesh of polyester and having a thickness of 70 μm and a mesh size of 40 um.

Example 2

A fourth model (model 4) of oxygenator was fabricated according to the construction shown in FIG. 19 (tenth embodiment). The construction is detailed in Table 1 below. The oxygenator has the first enlargement in a base of the blood outlet port as shown in FIG. 19. The hollow fiber membranes forming the hollow fiber membrane bundle and the filter member are similar to those of Example 1.

Comparative Example 1

Figure 20:
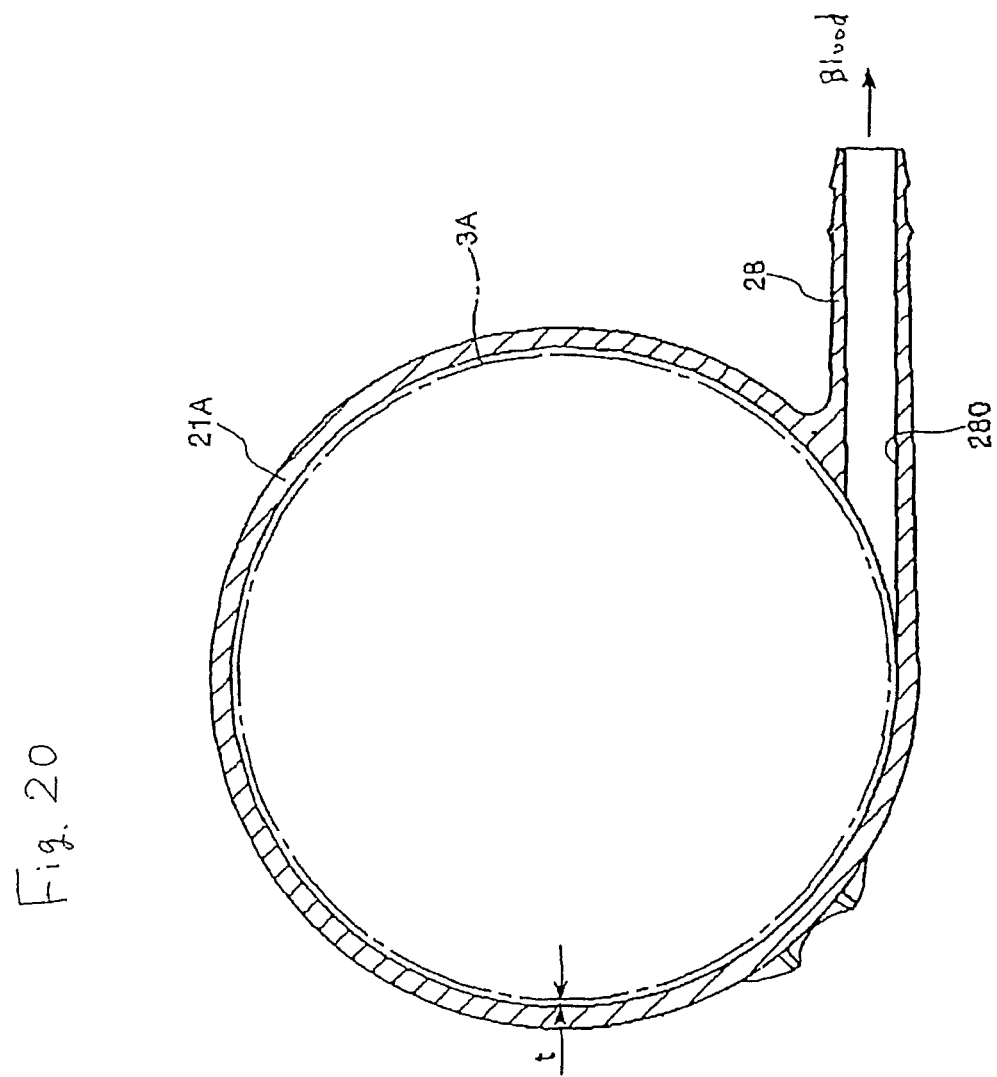
FIG. 20 is a cross-sectional view of a cylindrical housing body of an oxygenator in a comparative example.

As comparative examples, the oxygenators used were Capiox® RX25 (model 5), RX15 (model 6) and RX05 (model 7) marketed by Terumo Kabushiki Kaisha. A gas outlet fiber membrane layer and a filter member are absent. As shown in FIG. 20, the outer shell has an inner peripheral surface having a tangential line coincident with the inner surface of the blood outlet port. That is, in these Comparative Examples, a passage enlargement (second passage enlargement) is not existent. A first passage enlargement also is absent. The construction of these Comparative Examples is detailed in Table 1.

Comparative Example 2

Another oxygenator (model 8) similar to that of Comparative Example 1 was fabricated, except that a filter member the same in type as used in Example 1 was provided in the outer peripheral surface of the hollow fiber membrane bundle. The oxygenator of Comparative Example 2 (model 5) has the conditions or characteristics shown in Table 1.

Bubble Removal Performance Test

The following bubble removal performance test was conducted on the oxygenators (models 1-8) of Examples 1 and 2, and Comparative Examples 1 and 2.

The oxygenators of models 1-8 were each incorporated into a blood extracorporeal circulation circuit to circulate the blood of a test animal (cattle blood, hematocrit value=35%, blood temperature=37° C.) at a flow rate shown in Table 3. In a position immediately preceding the blood inlet port of the oxygenator, bubbles different in size and form were put into the blood. Using a bubble detector, measurement was made of the amount of bubbles in the blood flowing our of the blood outlet port under the conditions shown below. The result is shown in Table 2.

Bubble detection time: 1 minute

Bubble count: the bubbles measured by the bubble detector were classified according to classes at a bubble-size interval of 10 μM, to find the classified totals of bubbles.

TABLE 1

Oxygenator Specification

| | Example 1 | | | Example 2 | Comparative Example 1 | | | Comparative Example 2 |
| --- | --- | --- | --- | --- | --- | --- | --- | --- |
| | Model 1 | Model 2 | Model 3 | Model 4 | Model 5 RX25 | Model 6 RX15 | Model 7 RX05 | Model 8 |
| Inner diameter of oxygenator outer shell d[mm] | 108 | 107.5 | 75.56 | 108 | 108 | 107.5 | 75.56 | 108 |
| Outermost diameter of hollow fiber membrane bundle D[mm] | 105 | 105 | 73.8 | 105 | 105 | 105 | 73.8 | 105 |
| Effective length of hollow fiber membrane L[mm] | 90 | 52 | 28 | 90 | 90 | 52 | 28 | 90 |
| Presence/absence of filter member | Present | Present | Present | Present | Absent | Absent | Absent | Present |
| Presence/absence of passage enlargement (first enlargement/second enlargement) | Present/present | Present/present | Present/present | Present/absent | Absent/absent | Absent/absent | Absent/absent | Absent/absent |
| Gap size between filter member (or hollow fiber membrane bundle) and outer shell inner peripheral surface t [mm] | 1.5 | 1.25 | 0.88 | 1.5 | 1.5 | 1.25 | 0.88 | 1.5 |
| the first enlargement t1 [mm] | 2.75 | 2.75 | 1.88 | 2.75 | 1.5 | 1.25 | 0.88 | 1.5 |
| the second enlargement c [mm] | 1 | 1 | 1 | 0 | 0 | 0 | 0 | 0 |
| Passage area of the first enlargement (S = t1 × L) [cm$^2$] | 2.48 | 1.43 | 0.53 | 2.48 | 1.35 | 0.65 | 0.25 | 1.35 |
| Total flow rate of blood Q(=Q1 + Q2)[mL/min] | 7000 | 5000 | 1500 | 7000 | 7000 | 5000 | 1500 | 7000 |
| Flow rate of blood through clearance (semicircular) Q1 (=Q2)[mL/min] | 3500 | 2500 | 750 | 3500 | 3500 | 2500 | 750 | 3500 |
| Mean blood velocity (=Q1 ÷ S)[cm/min] | 1414 | 1748 | 1425 | 1414 | 2593 | 3846 | 3044 | 2593 |
| Mesh size of Filter member [μm] | 40 | 40 | 40 | 40 | — | — | — | 40 |
| Distance between filter member (or hollow fiber membrane bundle) and blood outlet port t2 [mm] | 3.75 | 3.75 | 2.88 | 2.75 | 1.5 | 1.25 | 0.88 | 1.5 |
| Condition of the first enlargement | | | | | | | | |
| Gap size increment Δt(=t1 − t) [mm] | 1.25 | 1.5 | 1 | 1.25 | — | — | — | — |
| First enlargement width (chord length) W [mm] | 66 | 66 | 37.5 | 66 | — | — | — | — |
| First enlargement depth (length longitudinal of outer shell) [mm] | 90 | 52 | 28 | 90 | — | — | — | — |

TABLE 2

Bubble Performance Test (Bubble count detected by bubble detector)

|  | Model | Flow rate of blood Q [mL/min] | Bubble size [µm] | | | | | |
|---|---|---|---|---|---|---|---|---|
|  |  |  | 41-50 | 51-60 | 61-70 | 71-80 | 81-90 | 91-100 |
| Example 1 | Model 1 | 7000 | 0 | 0 | 0 | 0 | 0 | 0 |
|  | Model 2 | 5000 | 0 | 0 | 0 | 0 | 0 | 0 |
|  | Model 3 | 1500 | 0 | 0 | 0 | 0 | 0 | 0 |
| Example 2 | Model 4 | 7000 | 1 | 0 | 0 | 0 | 0 | 0 |
| Comparative example 1 | Model 5 RX25 | 7000 | 32 | 56 | 34 | 9 | 1 | 0 |
|  | Model 6 RX15 | 5000 | 61 | 40 | 15 | 3 | 0 | 0 |
|  | Model 7 RX05 | 1500 | 106 | 72 | 44 | 27 | 5 | 0 |
| Comparative example 2 | Model 8 | 7000 | 13 | 9 | 7 | 3 | 0 | 0 |

[unit: bubble count]

As shown in Table 2, the oxygenators (models 1-4) in Examples 1 and 2 were observed to have a high bubble removal performance. Particularly, the oxygenators (models 1-3) in Example 1, having a passage enlargement formed by the first and second enlargements, possesses an extremely high bubble removal performance in which no bubbles, regardless of bubble size, were observed at the blood outlet port.

It is to be recognized that the principles, embodiments and modes of operation have been described in the foregoing specification, but the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A method of performing gas exchange for blood comprising:
   introducing blood into a housing in which are positioned a plurality of hollow fiber membranes each having a lumen so that the blood flows exteriorly of the hollow fiber membranes, the housing defining a blood flow path between a blood inlet and a blood outlet port;
   introducing gas into the lumens of the hollow fiber membranes and subjecting the blood flowing exteriorly of the hollow fiber membranes to gas exchange with the gas flowing through the lumens of the hollow fiber membranes;
   passing the blood through a filter member having a mesh size of approximately 15-60 µm, the filter member being positioned in the housing directly contacting the hollow fiber membranes at a position downstream of the hollow fiber membranes, thus removing bubbles in the blood while the blood is in the housing and after the blood has been subjected to the gas exchange;
   passing the blood through a blood passage downstream of the filter member, the blood passage being defined by a gap having a predetermined width between an outer surface of the filter member and an inner surface of the housing;
   passing the blood through a passage enlargement positioned between the blood passage and the blood outlet port, the passage enlargement having an enlarged width defined between the outer surface of the filter member and the inner surface of the housing, the enlarged width being greater than the predetermined width of the blood passage such that the passage enlargement provides an increased passage cross-sectional area relative to the blood passage, thereby decelerating the blood from which bubbles have been removed as the blood approaches the blood outlet port in the housing; and
   discharging from the housing by way of the blood outlet port the blood which has been decelerated.

2. A method according to claim 1, further comprising discharging bubbles which have been removed from the blood by way of lumens in hollow fiber membranes forming a gas outlet hollow fiber membrane layer.

3. A method according to claim 1, further comprising discharging bubbles which have been removed from the blood by way of the lumens of the hollow fiber membranes.

4. A method according to claim 1, wherein the passage enlargement includes a first enlargement and a second enlargement, said step of passing the blood through the passage enlargement includes the blood flowing along both the first and second enlargements before being discharged from the housing by way of the blood outlet port.

5. A method according to claim 4, wherein the first enlargement includes a groove formed in an inner surface of the housing and said step of passing the blood through the passage enlargement includes the blood flowing along the groove before being discharged from the housing by way of the blood outlet port.

6. A method according to claim 1, wherein the predetermined width of the gap between the outer surface of the filter member and the inner surface of the housing is defined parallel to a blood flow direction of the blood.

7. A method according to claim 1, further comprising passing the blood through a gas outlet hollow fiber membrane layer positioned in the housing at a position downstream of the hollow fiber membranes and upstream of the filter member.

8. A method according to claim 1, wherein the filter member is positioned in the housing and covers an entirety of the blood flow path, and passing the blood through the filter member includes passing all of the blood flowing in the blood flow path through the filter member.

* * * * *